(12) United States Patent
Tojo et al.

(10) Patent No.: US 9,079,836 B2
(45) Date of Patent: Jul. 14, 2015

(54) COMPOUND HAVING 2-FLUOROPHENYLOXYMETHANE STRUCTURE, A METHOD FOR PREPARING THE SAME, A LIQUID CRYSTAL COMPOSITION AND A LIQUID CRYSTAL DEVICE

(71) Applicant: DIC Corporation, Tokyo (JP)

(72) Inventors: Kenta Tojo, Kita-adachi-gun (JP); Tetsuo Kusumoto, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 14/346,498

(22) PCT Filed: Dec. 20, 2012

(86) PCT No.: PCT/JP2012/083070
§ 371 (c)(1),
(2) Date: Mar. 21, 2014

(87) PCT Pub. No.: WO2013/099754
PCT Pub. Date: Jul. 4, 2013

(65) Prior Publication Data
US 2014/0330045 A1    Nov. 6, 2014

(30) Foreign Application Priority Data

Dec. 26, 2011  (JP) ................................. 2011-283306

(51) Int. Cl.
| | | |
|---|---|---|
| *C07C 43/205* | (2006.01) | |
| *C07C 41/01* | (2006.01) | |
| *C07F 5/02* | (2006.01) | |
| *G02F 1/13* | (2006.01) | |
| *C09K 19/06* | (2006.01) | |
| *C09K 19/32* | (2006.01) | |
| *C07C 43/225* | (2006.01) | |
| *C09K 19/40* | (2006.01) | |
| *C07C 41/30* | (2006.01) | |

(52) U.S. Cl.
CPC ................. *C07C 41/01* (2013.01); *C07C 41/30* (2013.01); *C07C 43/225* (2013.01); *C07F 5/02* (2013.01); *C09K 19/062* (2013.01); *C09K 19/322* (2013.01); *C09K 19/404* (2013.01); *G02F 1/13* (2013.01)

(58) Field of Classification Search
USPC .......................................... 568/631, 634, 657
See application file for complete search history.

(56) References Cited

U.S. PATENT DOCUMENTS

| | | | |
|---|---|---|---|
| 2003/0236304 A1 | 12/2003 | Jolidon et al. | |
| 2010/0328600 A1* | 12/2010 | Shimada et al. | 349/182 |

FOREIGN PATENT DOCUMENTS

| | | |
|---|---|---|
| CN | 102186821 A | 9/2011 |
| JP | 02-501311 A | 5/1990 |
| JP | 02-233626 A | 9/1990 |
| JP | 04-501575 A | 3/1992 |
| JP | 06-504032 A | 5/1994 |
| JP | 09-157202 A | 6/1997 |
| JP | 10-101599 A | 4/1998 |
| JP | 2000-355560 A | 12/2000 |
| JP | 2005-517079 A | 6/2005 |
| JP | 2005-529176 A | 9/2005 |
| KR | 10-2006-0119879 A | 11/2006 |
| WO | 98/23564 A1 | 6/1998 |
| WO | 2005/019377 A1 | 3/2005 |
| WO | 2008/105286 A1 | 9/2008 |
| WO | 2009/034867 A1 | 3/2009 |
| WO | 2010/047260 A1 | 4/2010 |
| WO | 2012/161178 A1 | 11/2012 |

OTHER PUBLICATIONS

Interntioanal Search Report, dated Apr. 2, 2013, issued in corresponding application No. PCT/JP2012/083070.
Kuchar, Miroslav, et al., "Use of QSAR in Design of Antiinflammatory Fluorinated Arylalkanoic Acids", Collection of Czechoslovak Chemical Communications, 1990, vol. 55, No. 1, pp. 296-306.
Resistry(stn) [Online], Oct. 3, 2011, (retrieval date: Mar. 11, 2013 CAS resistration No. 1334226-61-7.

* cited by examiner

*Primary Examiner* — Sudhakar Katakam
*Assistant Examiner* — Pancham Bakshi
(74) *Attorney, Agent, or Firm* — Westerman, Hattori, Daniels & Adrian, LLP

(57) ABSTRACT

It is an object of the present invention to provide a compound having both a low viscosity (η) and good miscibility with another liquid crystal compound; it is another object of the present invention to provide a method for producing the same. It is another object of the present invention to provide a liquid crystal composition containing such a compound; it is another object of the present invention to provide a liquid crystal display device in which the compound is used.
There are provided a compound represented by Formula (1), a liquid crystal composition containing such a compound, a liquid crystal device in which this liquid crystal composition is used, a method for producing the compound represented by Formula (1), and compounds represented by Formulae (4) and (5) that are materials used in such a method.

17 Claims, No Drawings

COMPOUND HAVING 2-FLUOROPHENYLOXYMETHANE STRUCTURE, A METHOD FOR PREPARING THE SAME, A LIQUID CRYSTAL COMPOSITION AND A LIQUID CRYSTAL DEVICE

TECHNICAL FIELD

The present invention relates to a compound having a 2-fluorophenyloxymethane structure, the compound being useful as organic electronic materials, medicine, and agricultural chemicals, in particular, useful as the materials of liquid crystal display devices.

BACKGROUND ART

Liquid crystal display devices have been applied to, for example, watches, calculators, a variety of measuring equipment, panels used in automobiles, word processors, electronic notebooks, printers, computers, television sets, clocks, and advertising boards. Representative examples of types of liquid crystal display devices include a TN (twisted nematic) type, an STN (super twisted nematic) type, and a vertical alignment type and IPS (in-plane switching) type in which a TFT (thin film transistor) is used. Liquid crystal compositions used for such liquid crystal display devices need to satisfy the following requirements: being stable to external elements such as moisture, air, heat, and light; having a liquid crystal phase (nematic phase, smectic phase, and blue phase) in a broad temperature range mainly including room temperature as much as possible; having a low viscosity; and enabling a low driving voltage. Liquid crystal compositions need to have dielectric anisotropy ($\Delta\in$) and refractive index anisotropy ($\Delta n$) optimum to individual display devices.

A liquid crystal composition having positive $\Delta\in$ is used in horizontal alignment-type displays such as a TN type, an STN type, and an IPS type. In another type of driving that has been reported, molecules of a liquid crystal composition having positive $\Delta\in$ are vertically aligned in a state in which voltage is not applied, and then a horizontal electric field is applied for performing display. A demand for a liquid crystal composition having positive $\Delta\in$ has therefore further increased. In all types of driving, however, there have been demands for improvement of response speed, and a liquid crystal composition having a lower viscosity than typical liquid crystal compositions is needed to satisfy such demands. In order to develop the liquid crystal composition having a low viscosity, it is effective to decrease the viscosity of individual compounds contained in a liquid crystal composition. In the case where a liquid crystal composition is applied to, for example, display devices, the liquid crystal composition needs to exhibit a liquid crystal phase stable in a broad temperature range.

In general, in terms of production of a compound having a low viscosity, it has been believed that the compound preferably has a molecular framework in which multiple cyclic structures are directly bonded to each other via no linking group, namely a structure called directly connected rings. Compounds having positive $\Delta\in$ and a structure in which three or more rings are directly connected to each other are generally highly crystalline; in the case where a liquid crystal composition containing such a compound is cooled, the crystals of this compound precipitate, which is problematic. A compound, for example, having the following fluorinated naphthalene structure (see Patent Literature 1)

[Chem. 1]

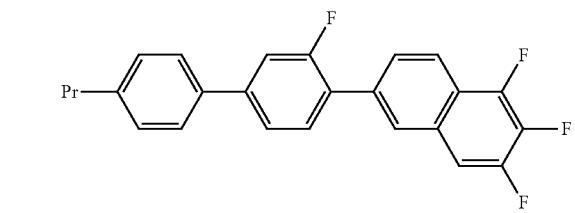

has large $\Delta\in$ and $\Delta n$ and relatively low viscosity; however, the crystals thereof precipitate depending on the constitution of a liquid crystal composition. In order to enhance solubility, a variety of compounds into which linking groups are introduced have been studied. Although the introduction of linking groups increases viscosity to some extent, miscibility in a liquid crystal composition can be enhanced (see Patent Literatures 2 to 9). A compound having a —CH$_2$O— group as a linking group is highly chemically stable, and a liquid crystal composition containing such a compound exhibits a liquid crystal phase stable in a broad temperature range; however, the viscosity of this liquid crystal composition is extraordinarily high, which is problematic.

In order to enhance the $\Delta\in$ of a liquid crystal composition, a polar compound having large $\Delta\in$ needs to be added to the liquid crystal composition in a high percentage. An increase in the amount of one polar compound to be contained, however, readily leads to generation of precipitates from the liquid crystal compound, and the upper limit of the amount in which the polar compound can be added is therefore determined. In a technique generally used for addressing such a problem, multiple compounds having a difference not in the basic skeleton but merely in the length of the alkyl chain are used to increase the polar compound content and to reduce precipitates. In this case, needless to say, analogous polar compounds having a difference only in the length of the alkyl side chain need to be produced at low costs, and an efficient synthetic route need to be determined. Hence, it is effective that the same synthetic intermediate be used and that a reaction route which enables a high yield be selected.

CITATION LIST

Patent Literature

PTL 1: Japanese Unexamined Patent Application Publication No. 2000-355560
PTL 2: Japanese Unexamined Patent Application Publication No. 10-101599
PTL 3: Japanese Unexamined Patent Application Publication (Translation of PCT Application) No. 2-501311
PTL 4: Japanese Unexamined Patent Application Publication No. 9-157202
PTL 5: Japanese Unexamined Patent Application Publication (Translation of PCT Application) No. 2005-517079
PTL 6: Japanese Unexamined Patent Application Publication No. 2-233626
PTL 7: Japanese Unexamined Patent Application Publication (Translation of PCT Application) No. 4-501575
PTL 8: Japanese Unexamined Patent Application Publication (Translation of PCT Application) No. 6-504032
PTL 9: WO98/23564

SUMMARY OF INVENTION

Technical Problem

It is an object of the present invention to provide a compound having both a low viscosity (η) and good miscibility with another liquid crystal compound; it is another object of the present invention to provide a method for producing the same. It is another object of the present invention to provide a liquid crystal composition containing such a compound; it is another object of the present invention to provide a liquid crystal display device in which the compound is used.

Solution to Problem

The inventors have studied a variety of compounds to achieve the above-mentioned objects and found that a compound having a 2-fluorophenyloxymethane structure effectively enables the objects to be achieved; furthermore, the inventors have studied an intermediate useful for efficient synthesis of such a compound and a method for producing the same, thereby accomplishing the present invention.

In order to produce an intended 2-fluorophenyloxymethane derivative, a compound represented by Formula (2)

[Chem. 2]

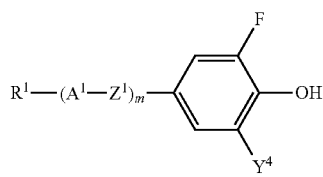

(2)

(where $R^1$ represents an alkyl group having 1 to 15 carbon atoms or an alkenyl group having 2 to 15 carbon atoms in which one —$CH_2$— moiety or at least two —$CH_2$— moieties not adjoining each other are each independently optionally substituted with —O—, —S—, —COO—, —OCO—, or —CO—, $A^1$ is a group selected from the group consisting of (a) a 1,4-cyclohexylene group (where one —$CH_2$— moiety or at least two —$CH_2$— moieties not adjoining each other are each independently optionally substituted with O— or —S—) and
(b) a 1,4-phenylene group (where one —CH= moiety or at least two —CH= moieties not adjoining each other are optionally substituted with —Na=, and a hydrogen atom is optionally substituted with a fluorine atom),
$Z^1$ represents —$CH_2O$—, —$OCH_2$—, —$CF_2O$—, —$OCF_2$—, —$CH_2CH_2$—, —$CF_2CF_2$—, —CH=CH—, —CF=CF—, —C≡C—, or a single bond,
$Y^4$ represents a hydrogen atom, a fluorine atom, or a chlorine atom, and
m represents 0 or 1) is allowed to react with a compound represented by Formula (3)

[Chem. 3]

$$X^1\text{—}CH_2\text{-}(A^2\text{-}Z^2)_n\text{-}A^3\text{-}X^2 \quad (3)$$

(where $A^2$ represents the same as $A^1$ in Formula (2), $A^3$ represents a 1,4-phenylene group (where a hydrogen atom is optionally substituted with a fluorine atom), $X^1$ represents a hydroxyl group, a chlorine atom, a bromine atom, an iodine atom, a tosyloxy group, a mesyloxy group, or a trifluoromethanesulfonyloxy group,
$X^2$ represents a chlorine atom, a bromine atom, or an iodine atom or is optionally a hydrogen atom in the case where $A^3$ is a group selected from (A-1) or (A-2),

[Chem. 4]

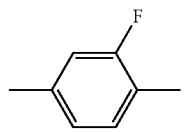

(A-1)

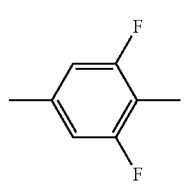

(A-2)

$Z^2$ represents the same as $Z^1$ in Formula (2), and n represents 0 or 1.) to derive a compound represented by Formula (4), where in the case where $X^1$ is a hydroxyl group, the reaction of the compound represented by Formula (2) with the compound represented by Formula (3) is condensation in the presence of a dehydrating condensation agent, and in the case where $X^1$ is a chlorine atom, a bromine atom, an iodine atom, a tosyloxy group, a mesyloxy group, or a trifluoromethanesulfonyloxy group, the reaction is an etherification reaction in the presence of a base,

[Chem. 5]

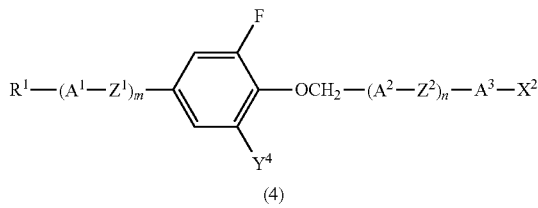

(4)

(where $R^1$, $A^1$, $A^2$, $A^3$, $Z^1$, $Z^2$, m, n, $Y^4$, and $X^2$ each independently represent the same as $R^1$, $A^1$, $A^2$, $A^3$, $Z^1$, $Z^2$, m, n, $Y^4$, and $X^2$ in Formula (2) or Formula (3)); a compound represented by Formula (5) is prepared through allowing the compound represented by Formula (4) to react with metal or organic metal and optionally further substituting the metal of a prepared organometallic compound with another atom

[Chem. 6]

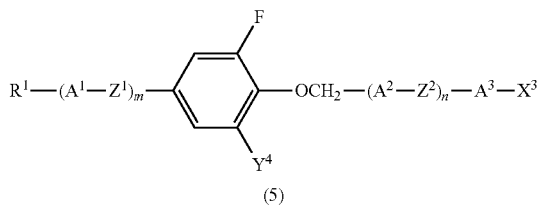

(5)

(where $R^1$, $A^1$, $A^2$, $A^3$, $Z^1$, $Z^2$, m, n, and $Y^4$ each independently represent the same as $R^1$, $A^1$, $A^2$, $A^3$, $Z^1$, $Z^2$, m, n, and $Y^4$ in Formula (4), and $X^3$ represents $MgX^4$, Li, Na, $ZnX^4$, or $CuX^4$ (where $X^4$ represents a chlorine atom, a bromine atom, or an iodine atom) or a substituent represented by Formula (B-1) or (B-2)

[Chem. 7]

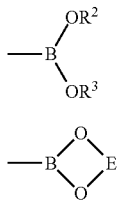

(B-1)

(B-2)

(where $R^2$ and $R^3$ each independently represent a linear or branched alkyl group having 1 to 5 carbon atoms, E represents —$(CH_2)_p$— in which one or more hydrogen atoms are each independently optionally substituted with a methyl group, and p represents 2, 3, or 4)); and the compound represented by Formula (5) is allowed to react with a compound represented by Formula (6)

[Chem. 8]

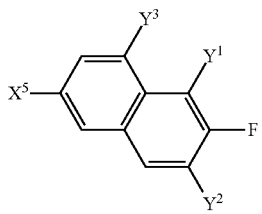

(6)

(where $Y^1$, $Y^2$, and $Y^3$ each independently represent a hydrogen atom, a fluorine atom, or a chlorine atom, and $X^5$ represents a trifluoromethanesulfonyloxy group, a chlorine atom, a bromine atom, or an iodine atom) in the presence of a transition metal catalyst to produce a compound represented by Formula (1)

[Chem. 9]

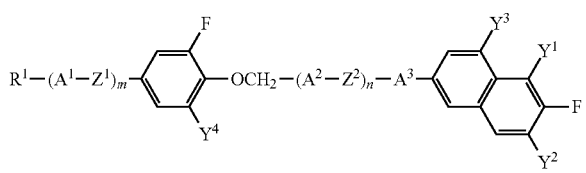

(1)

(where $R^1$, $A^1$, $A^2$, $A^3$, $Z^1$, $Z^2$, m, n, $Y^1$, $Y^2$, $Y^3$, and $Y^4$ each independently represent the same as $R^1$, $A^1$, $A^2$, $A^3$, $Z^1$, $Z^2$, m, n, $Y^1$, $Y^2$, $Y^3$, and $Y^4$ in Formula (5) or (6)). In addition, a liquid crystal composition containing such a compound and a liquid crystal display device in which this liquid crystal composition is used are provided.

Advantageous Effects of Invention

A compound represented by Formula (1) according to the present invention can be produced via compounds represented by Formula (4) or (5), and thus production thereof is industrially efficient. In addition, the compound represented by Formula (1) has both a low viscosity and good miscibility with another liquid crystal compound.

Accordingly, use of the compound represented by Formula (1) as a material of a liquid crystal composition enables a liquid crystal composition having a low viscosity and exhibiting a liquid crystal phase in a broad temperature range to be produced at low costs. Hence, such a compound is highly useful as a component of a liquid crystal composition used in a liquid crystal device which needs to quickly respond.

DESCRIPTION OF EMBODIMENTS

In order to efficiently produce a compound represented by Formula (1), it is preferred that the compound be produced via a compound represented by Formula (4) or a compound represented by Formula (5).

The compound represented by Formula (4) can be produced through the reaction of a compound represented by Formula (2) with a compound represented by Formula (3)

[Chem. 10]

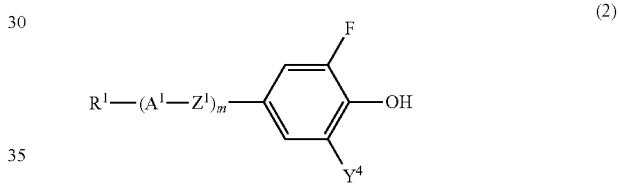

(2)

(where $R^1$ represents an alkyl group having 1 to 15 carbon atoms or an alkenyl group having 2 to 15 carbon atoms in which one —$CH_2$— moiety or at least two —$CH_2$— moieties not adjoining each other may be each independently substituted with —O—, —S—, —COO—, —OCO—, or —CO—;

$A^1$ is a group selected from the group consisting of (a) a 1,4-cyclohexylene group (where one —$CH_2$— moiety or at least two —$CH_2$— moieties not adjoining each other may be each independently substituted with O— or —S—)

(b) a 1,4-phenylene group (where one —CH= moiety or at least two —CH= moieties not adjoining each other may be each independently substituted with —Na, and a hydrogen atom may be substituted with a fluorine atom);

$Z^1$ represents —$CH_2O$—, —$OCH_2$—, —$CF_2O$—, —$OCF_2$—, —$CH_2CH_2$—, —$CF_2CF_2$—, —CH=CH—, —CF=CF—, —C≡C—, or a single bond;

$Y^4$ represents a hydrogen atom, a fluorine atom, or a chlorine atom; and m represents 0 or 1)

[Chem. 11]

(3)

(where $A^2$ represents the same as $A^1$ in Formula (2);

$A^3$ represents a 1,4-phenylene group (where a hydrogen atom may be substituted with a fluorine atom);

$X^1$ represents a hydroxyl group, a chlorine atom, a bromine atom, an iodine atom, a tosyloxy group, a mesyloxy group, or a trifluoromethanesulfonyloxy group;

$X^2$ represents a chlorine atom, a bromine atom, or an iodine atom or may be a hydrogen atom in the case where $A^3$ is a group selected from (A-1) or (A-2);

[Chem. 12]

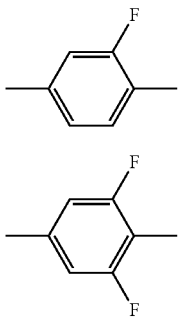

(A-1)

(A-2)

$Z^2$ represents the same as $Z^1$ in Formula (2); and n represents 0 or 1.). In the production of the compound represented by Formula (4), in the case where $X^1$ is a hydroxyl group, the reaction of the compound represented by Formula (2) with the compound represented by Formula (3) is condensation in the presence of a dehydrating condensation agent, and in the case where $X^1$ is a chlorine atom, a bromine atom, an iodine atom, a tosyloxy group, a mesyloxy group, or a trifluoromethanesulfonyloxy group, the reaction is an etherification reaction in the presence of a base

[Chem. 13]

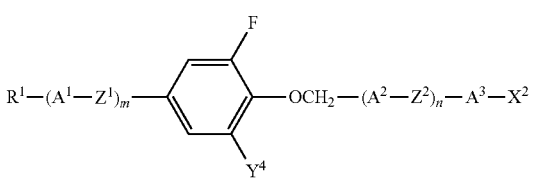

(4)

(where $R^1$, $A^1$, $A^2$, $A^3$, $Z^1$, $Z^2$, m, n, $Y^4$, and $X^2$ each independently represent the same as $R^1$, $A^1$, $A^2$, $A^3$, $Z^1$, $Z^2$, m, n, $Y^4$, and $X^2$ in Formula (2) or Formula (3)). In view of a yield in the etherification reaction, $X^1$ is preferably a bromine atom, an iodine atom, or, a mesyloxy group. In consideration of reactivity in the subsequent process, $X^2$ is preferably a hydrogen atom, a bromine atom, or an iodine atom.

Then, the compound represented by Formula (4) is allowed to react with metal or organic metal, or the metal of the resulting organometallic compound is further substituted with another atom, thereby preparing a compound represented by Formula (5)

[Chem. 14]

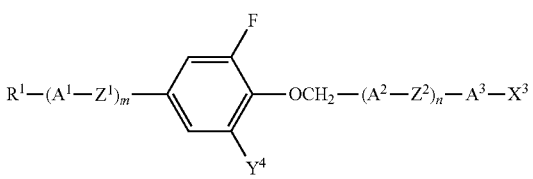

(5)

(where $R^1$, $A^1$, $A^2$, $A^3$, $Z^1$, $Z^2$, m, n, and $Y^4$ each independently represent the same as $R^1$, $A^1$, $A^2$, $A^3$, $Z^1$, $Z^2$, m, n, and $Y^4$ in Formula (4); and $X^3$ represents $MgX^4$, Li, Na, $ZnX^4$, or $CuX^4$ (where $X^4$ represents a chlorine atom, a bromine atom, or an iodine atom) or represents a substituent represented by Formula (B-1) or (B-2)

[Chem. 15]

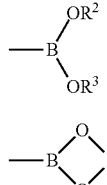

(B-1)

(B-2)

(where $R^2$ and $R^3$ each independently represent a linear or branched alkyl group having 1 to 5 carbon atoms,
E represents —$(CH_2)_p$— in which one or more hydrogen atoms may be each independently substituted with a methyl group, and
p represents 2, 3, or 4)).

In view of a yield in the subsequent process, $X^3$ is preferably $MgX^4$ or $ZnX^4$ in which $X^4$ is a bromine atom or a chlorine atom, a substituent represented by Formula (B-1) in which $R^2$ and $R^3$ are hydrogen atoms, or a substituent represented by Formula (B-2) in which p is 2 or 3.

Then, the compound represented by Formula (5) is allowed to react with a compound represented by Formula (6)

[Chem. 16]

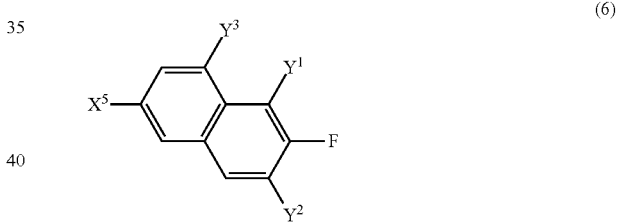

(6)

(where $Y^1$, $Y^2$, and $Y^3$ each independently represent a hydrogen atom, a fluorine atom, or a chlorine atom; and
$X^5$ represents a trifluoromethanesulfonyloxy group, a chlorine atom, a bromine atom, or an iodine atom) in the presence of a transition metal catalyst to yield a compound represented by Formula (1)

[Chem. 17]

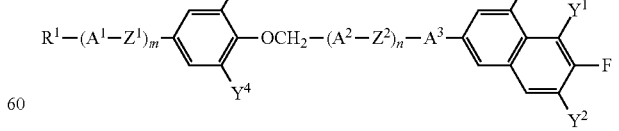

(1)

(where $R^1$, $A^1$, $A^2$, $A^3$, $Z^1$, $Z^2$, m, n, $Y^1$, $Y^2$, $Y^3$, and $Y^4$ each independently represent the same as $R^1$, $A^1$, $A^2$, $A^3$, $Z^1$, $Z^2$, m, n, $Y^1$, $Y^2$, $Y^3$, and $Y^4$ in Formula (5) or (6)). In view of a yield in this reaction, $X^5$ is preferably a trifluoromethanesulfonyloxy group, an iodine atom, or a bromine atom.

In Formula (1), in order to decrease the viscosity, $R^1$ is preferably an alkyl group having 1 to 8 carbon atoms or an alkenyl group having 2 to 8 carbon atoms, and especially preferably an alkyl group having 1 to 5 carbon atoms or an alkenyl group having 2 to 5 carbon atoms. In addition, the structure is preferably linear.

In order to decrease the viscosity, $A^1$ and $A^2$ are preferably each independently a trans-1,4-cyclohexylene group or an unsubstituted 1,4-phenylene group, more preferably a trans-1,4-cyclohexylene group; in order to enhance $\Delta\in$, $A^1$ and $A^2$ are preferably selected from the following groups.

[Chem. 18]

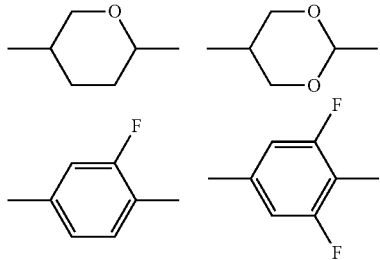

In order to enhance the solubility, the following groups

[Chem. 19]

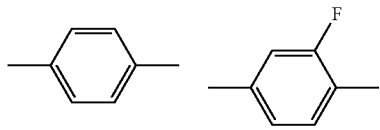

are preferred.

In order to enhance $\Delta\in$, $A^3$ is preferably selected from the following groups.

[Chem. 20]

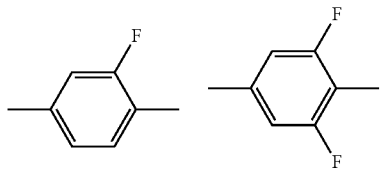

In order to decrease the viscosity, $A^3$ is preferably a 1,4-phenylene group unsubstituted with a fluorine atom; in order to enhance the solubility, the following groups

[Chem. 21]

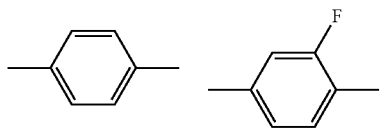

are preferred.

In order to decrease the viscosity, $Z^1$ and $Z^2$ are preferably each independently —CH$_2$O—, —OCH$_2$—, —CF$_2$O—, —OCF$_2$—, —CF=CF—, or a single bond, and more preferably —CF$_2$O—, —OCF$_2$—, —CH$_2$O—, —OCH$_2$—, or a single bond.

In order to decrease the viscosity, $Y^4$ is preferably a hydrogen atom or a fluorine atom; a fluorine atom is preferred in terms of an enhancement in $\Delta\in$, and a fluorine atom is preferred also in terms of an enhancement in the solubility.

In order to decrease the viscosity, $Y^1$, $Y^2$, and $Y^3$ are preferably each independently a hydrogen atom; in order to enhance $\Delta\in$, at least two of them are preferably fluorine atoms, and all of them are more preferably fluorine atoms. In order to enhance the solubility, at least one of them is preferably a hydrogen atom, and all of them are more preferably hydrogen atoms.

m is preferably 0 in view of the viscosity, preferably 1 in terms of an enhancement in $\Delta\in$, and preferably 0 in terms of an enhancement in the solubility. n is preferably 0 in view of the viscosity, preferably 1 in terms of an enhancement in $\Delta\in$, and preferably 0 in terms of an enhancement in the solubility.

The compound represented by Formula (1) does not have a structure in which hetero atoms are directly connected to each other.

Preferred examples of such a compound will now be specifically described; however, the compound of the present invention is not limited thereto. Preferred examples of the compound represented by Formula (1) include compounds represented by Formulae (1-1) to (1-103):

[Chem. 22]

(1-1)

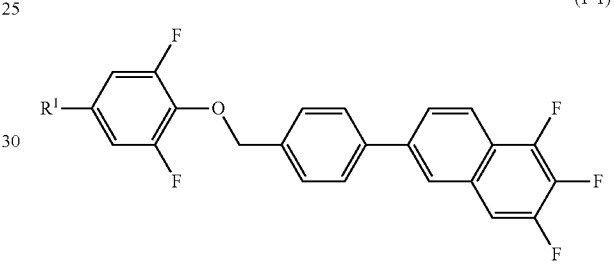

(1-2)

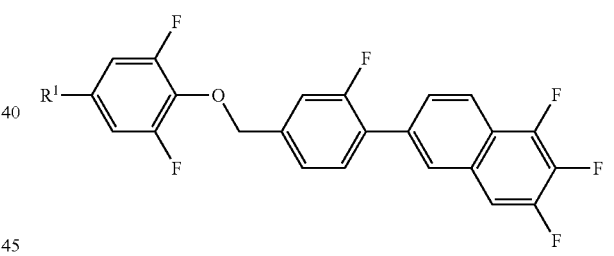

(1-3)

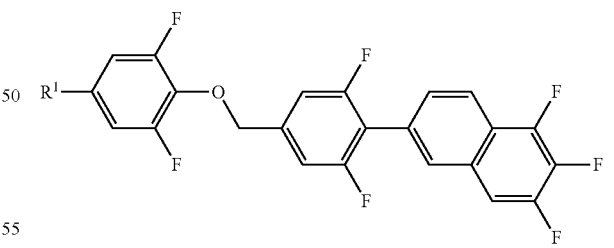

(1-4)

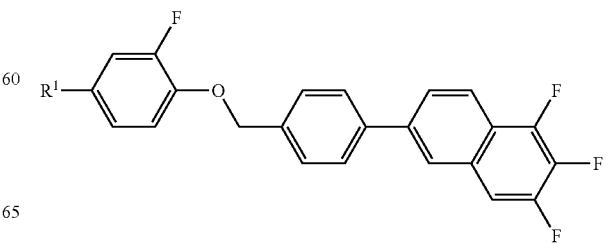

(1-5)
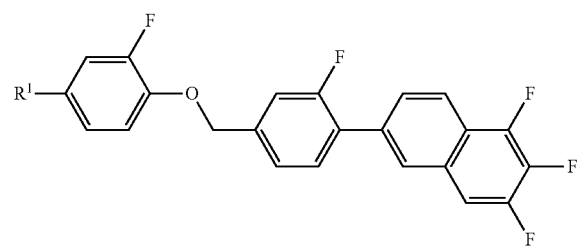
(1-11)
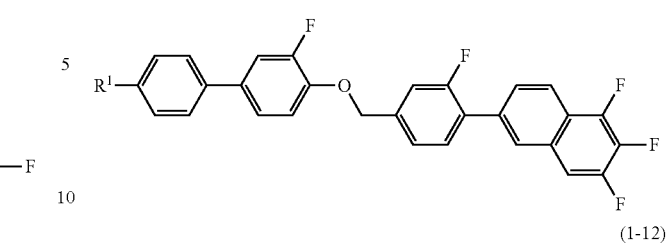
(1-6)
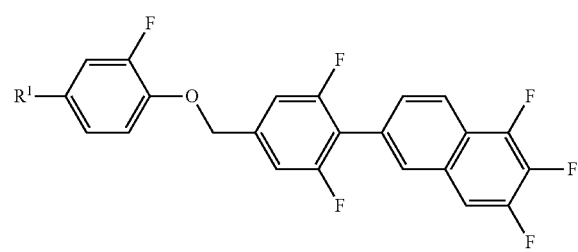
(1-12)
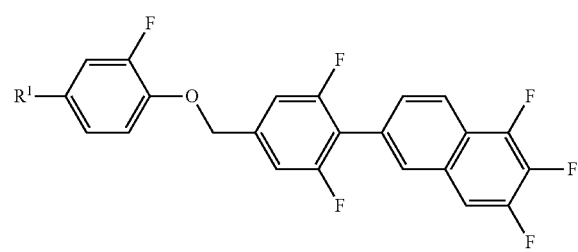
(1-7)
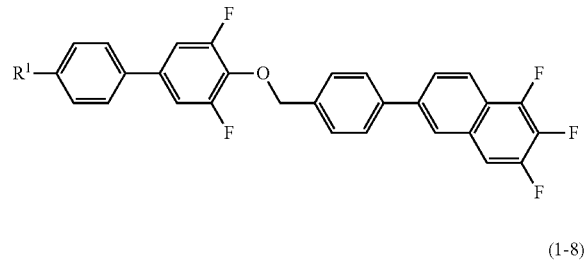
(1-13)
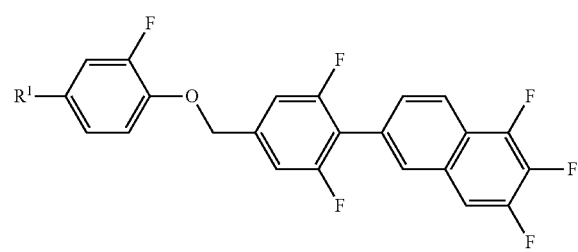
(1-14)
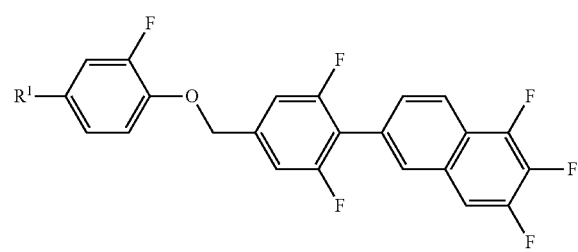
(1-8)
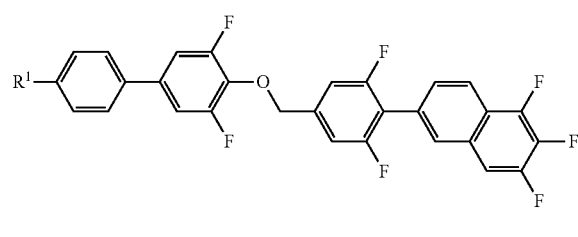
(1-15)
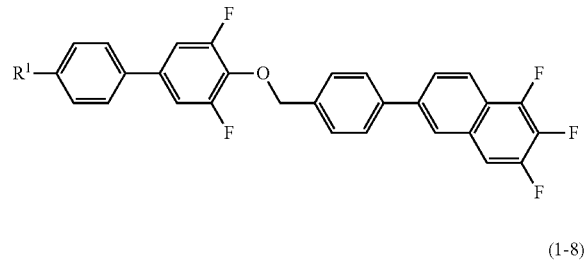
(1-9)
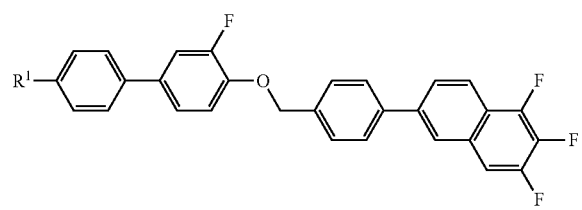
(1-16)
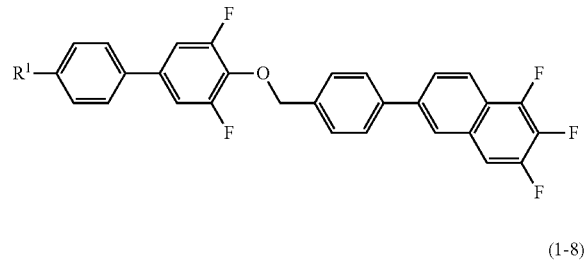
[Chem. 23]
(1-10)
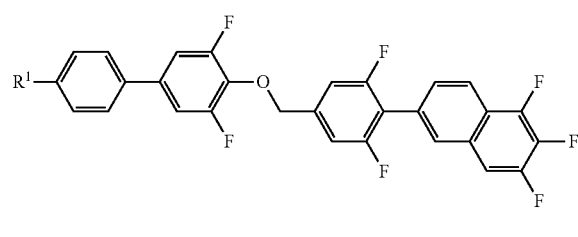
(1-17)
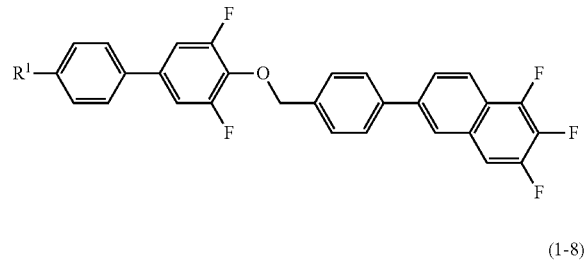

(1-18)
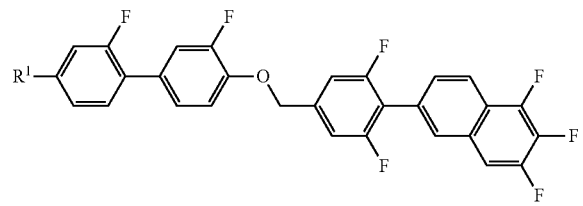
[Chem. 24]
(1-19)
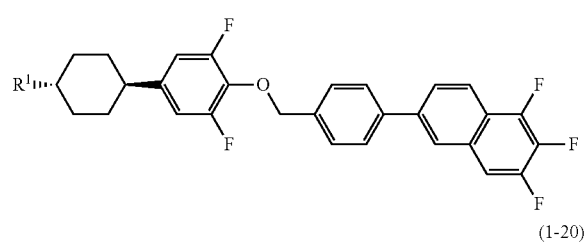
(1-20)
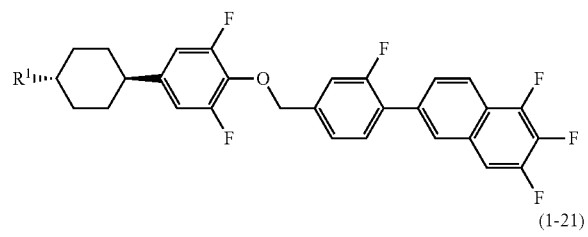
(1-21)
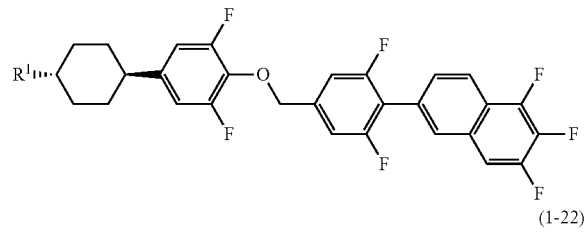
(1-22)
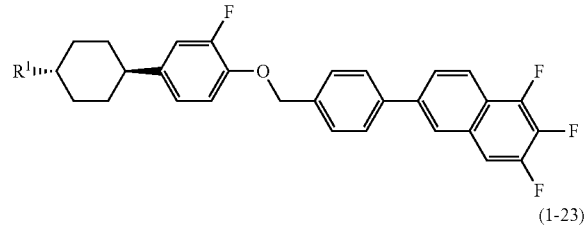
(1-23)
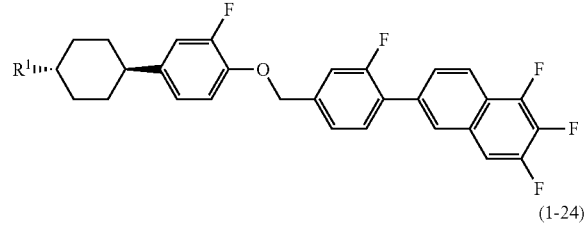
(1-24)
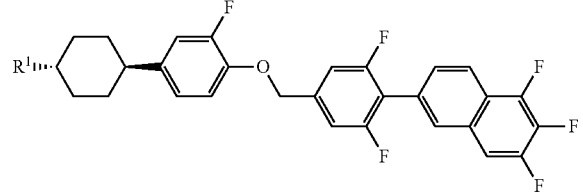
(1-25)
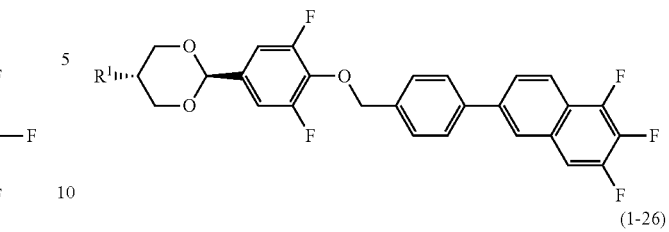
(1-26)
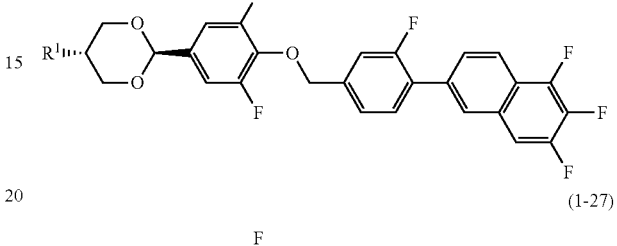
(1-27)
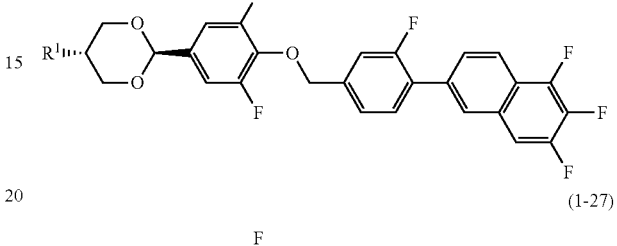
[Chem. 25]
(1-28)
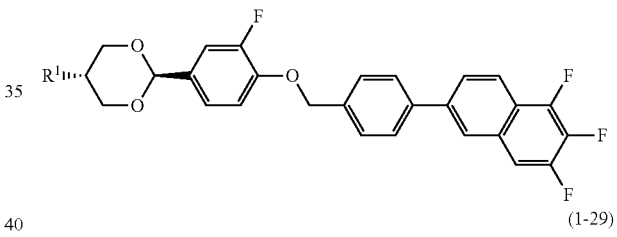
(1-29)
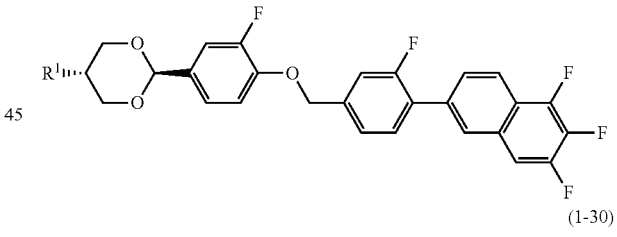
(1-30)
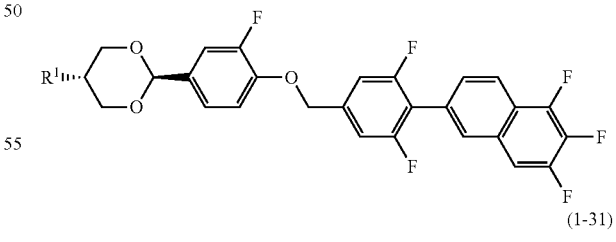
(1-31)
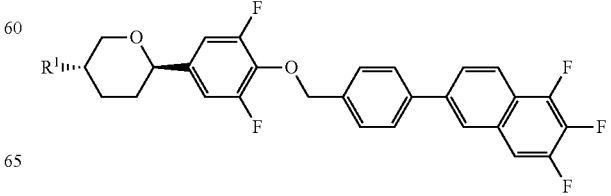

(1-32)
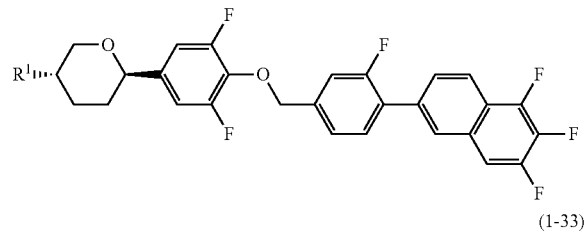
(1-39)
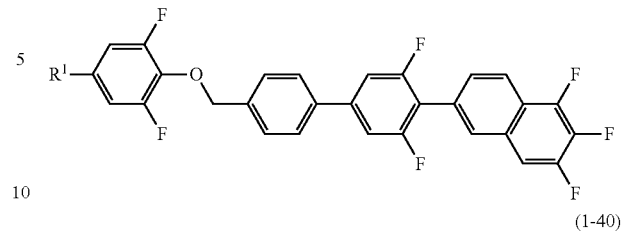
(1-33)
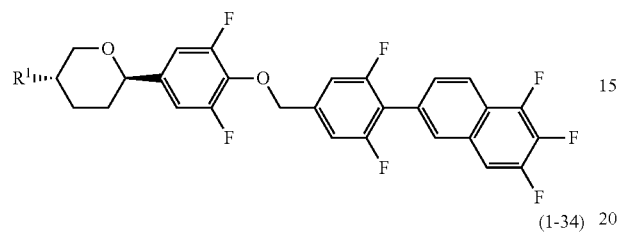
(1-40)
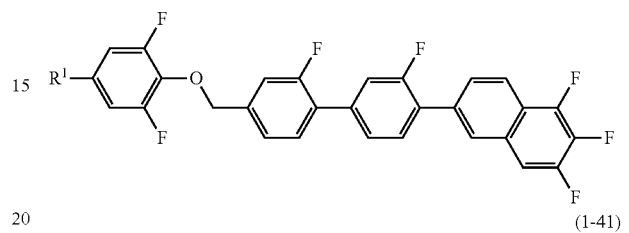
(1-34)
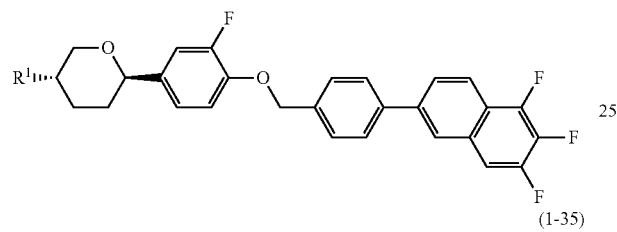
(1-41)
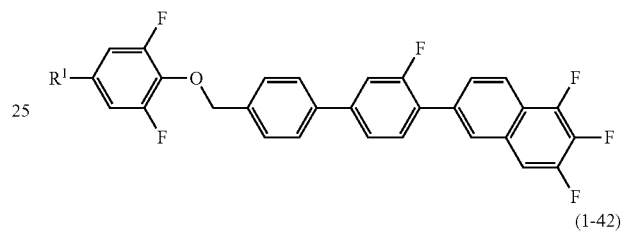
(1-35)
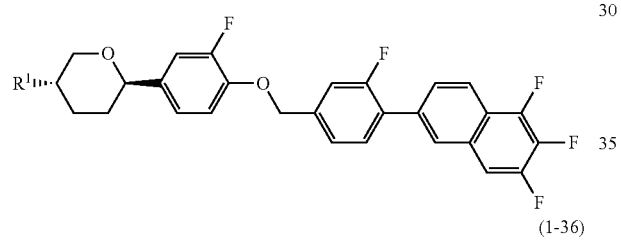
(1-42)
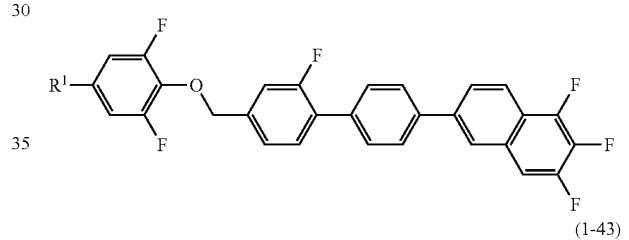
(1-36)
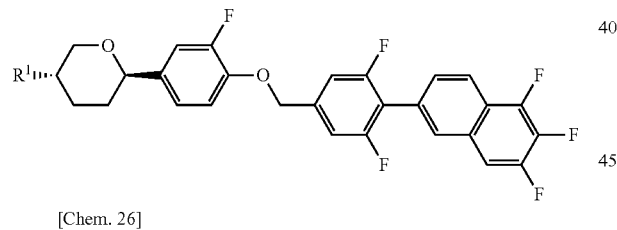
(1-43)
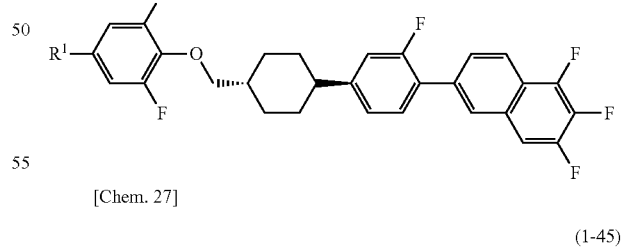
[Chem. 26]
(1-37)
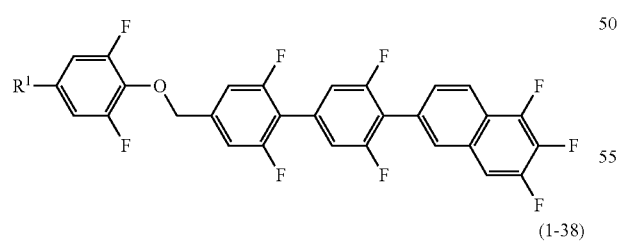
(1-44)
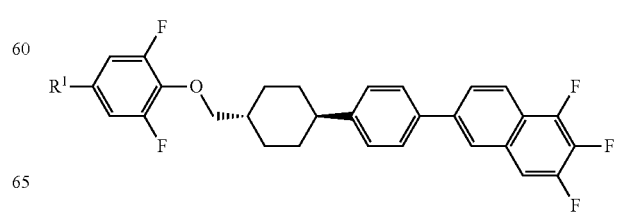
[Chem. 27]
(1-38)
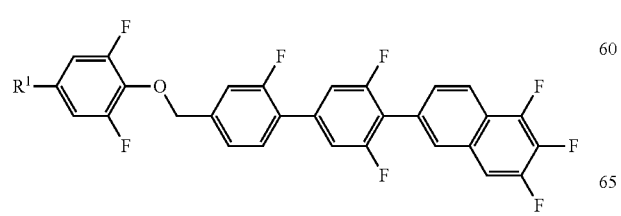
(1-45)

(1-46)
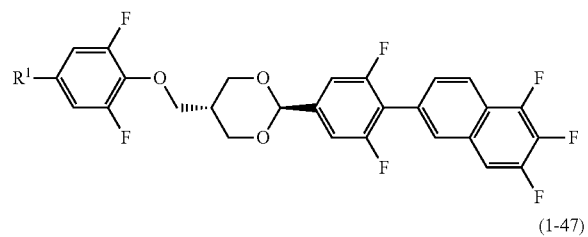
(1-47)
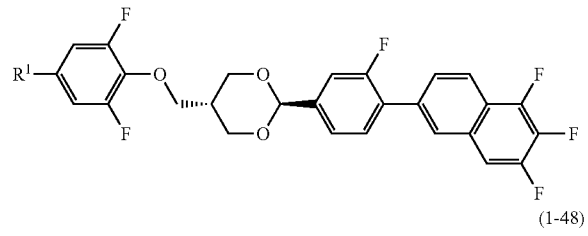
(1-48)
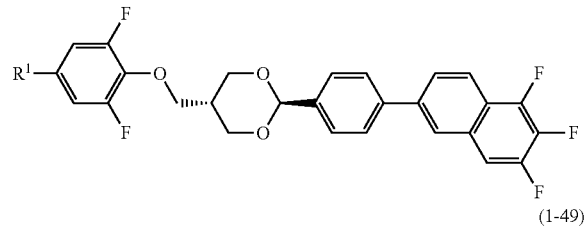
(1-49)
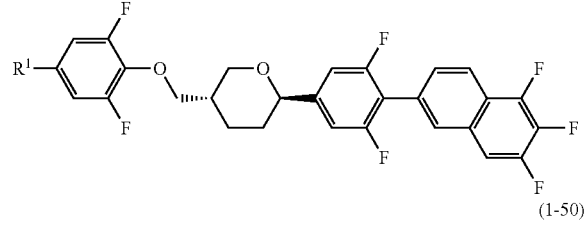
(1-50)
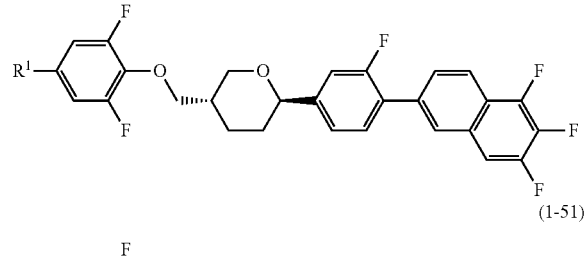
(1-51)
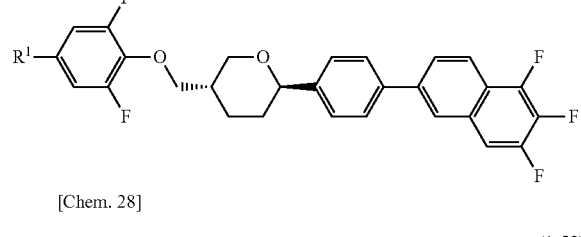
[Chem. 28]
(1-52)
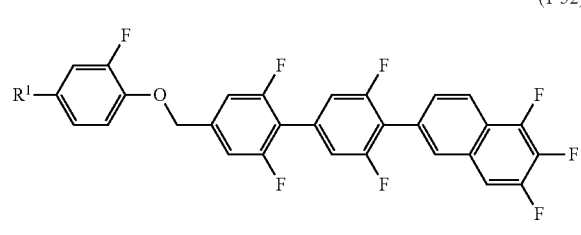
(1-53)
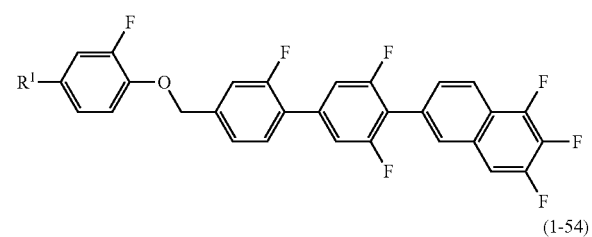
(1-54)
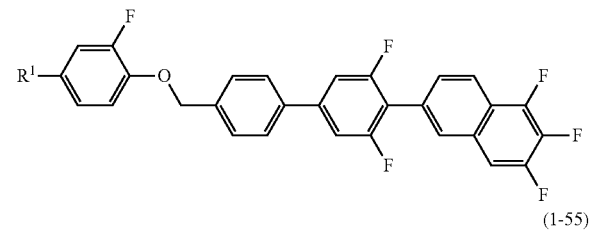
(1-55)
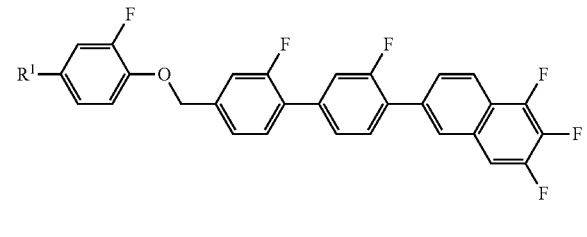
(1-56)
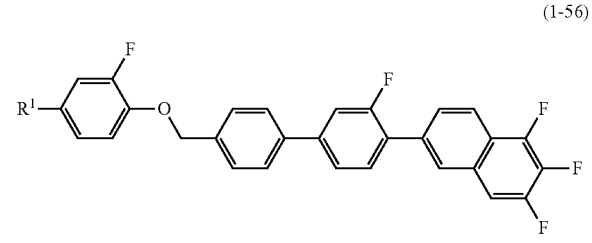
(1-57)
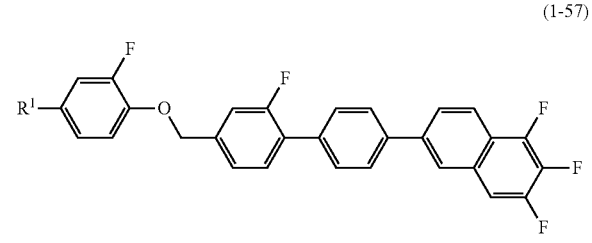
(1-58)
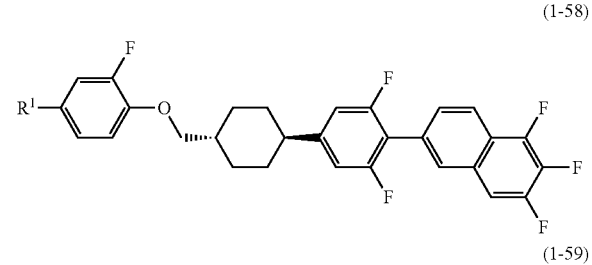
(1-59)

[Chem. 29]
(1-60)
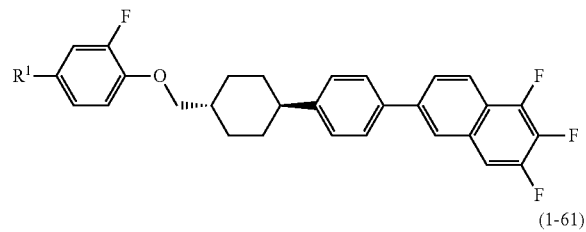
(1-61)
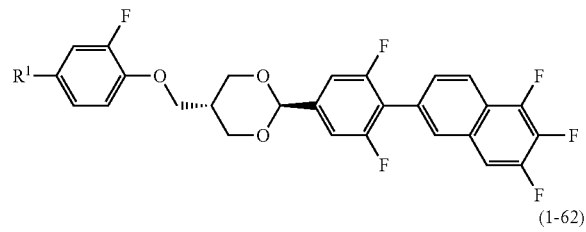
(1-62)
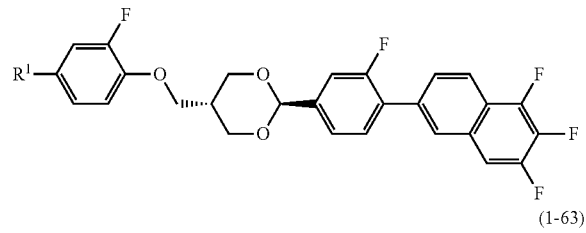
(1-63)
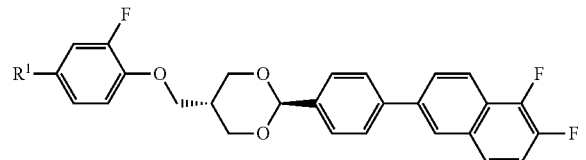
(1-64)
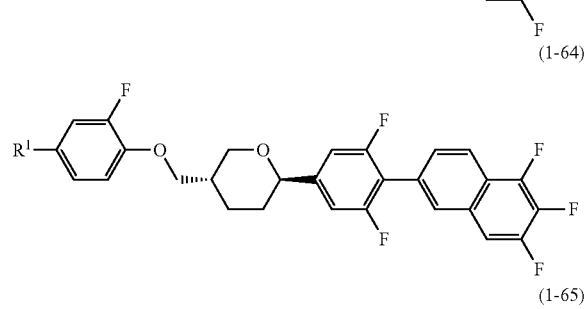
(1-65)
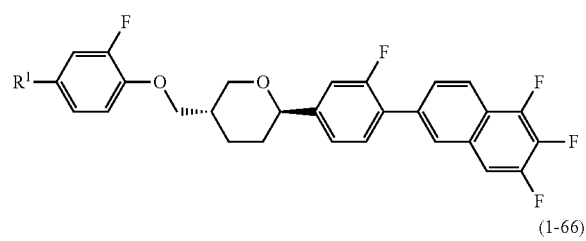
(1-66)
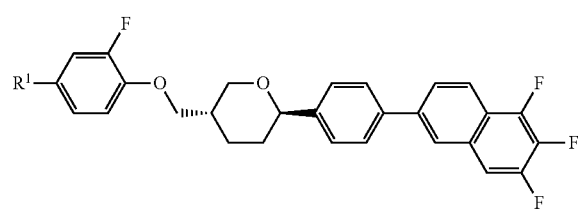
[Chem. 30]
(1-67)
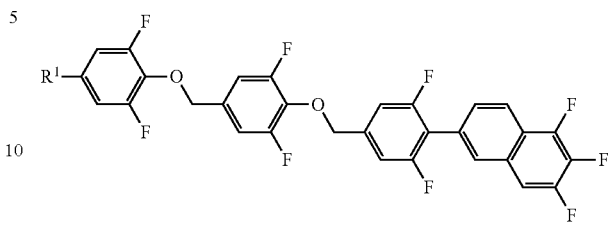
(1-68)
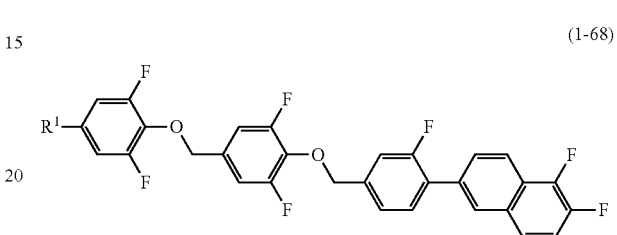
(1-69)
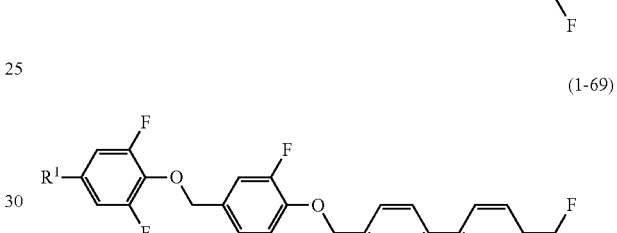
(1-70)
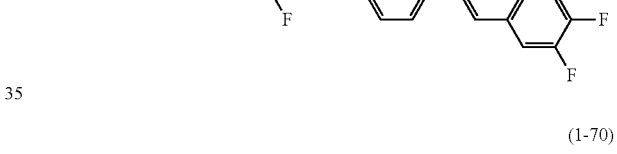
(1-71)
(1-72)
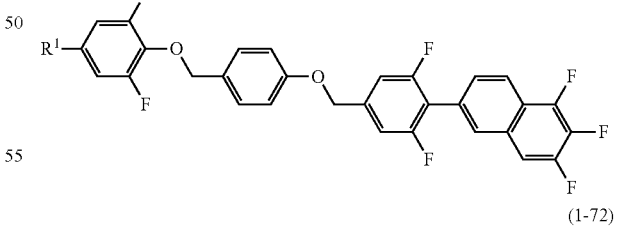

(1-73)
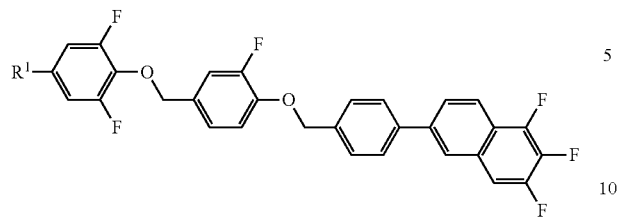
(1-74)
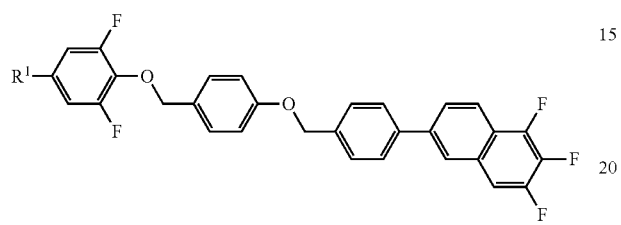
(1-75)
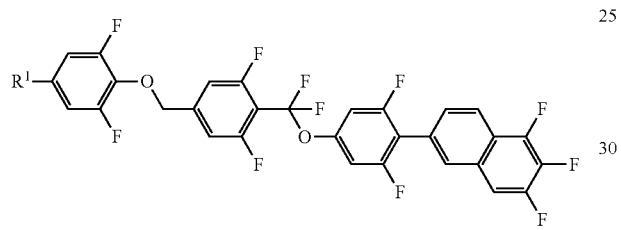
[Chem. 31]
(1-76)
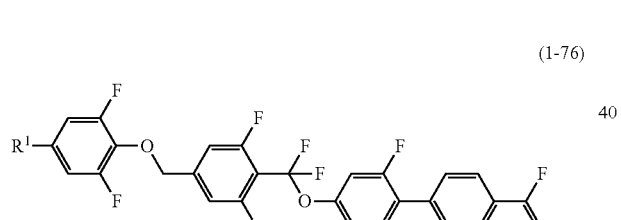
(1-77)
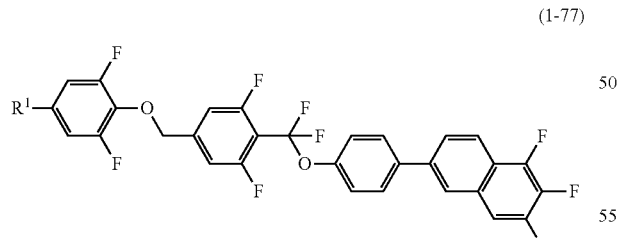
(1-78)
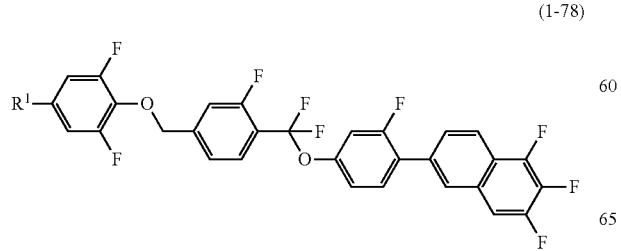
(1-79)
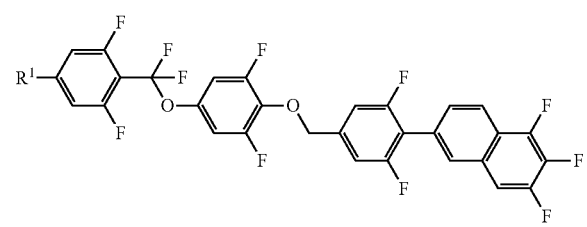
(1-80)
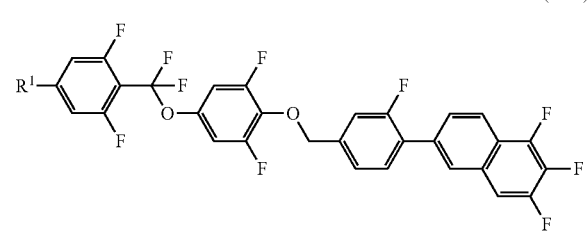
(1-81)
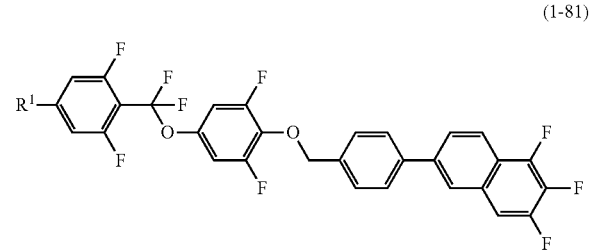
(1-82)
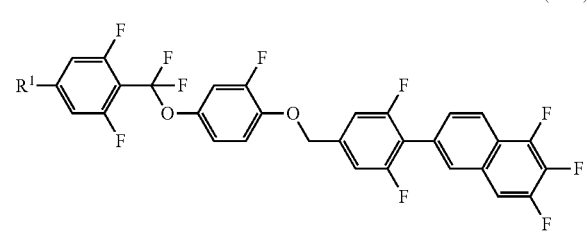
(1-83)
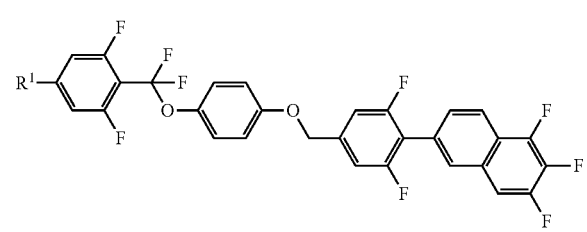
(1-84)
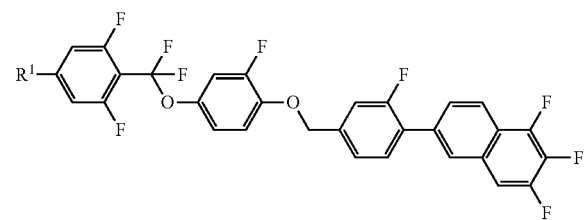

[Chem. 32]
(1-85)
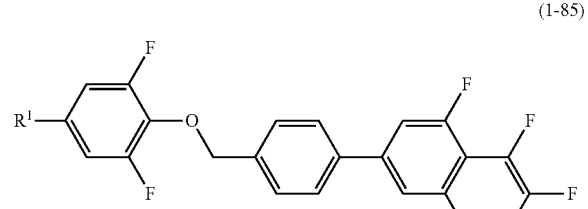
(1-86)
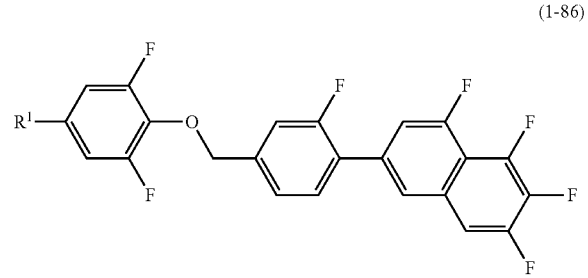
(1-87)
(1-88)
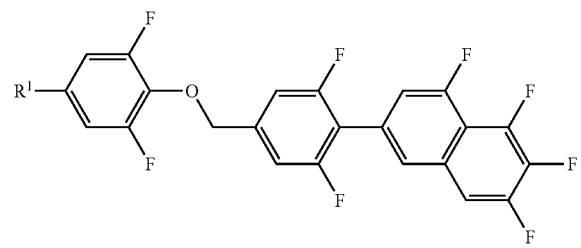
(1-89)
(1-90)
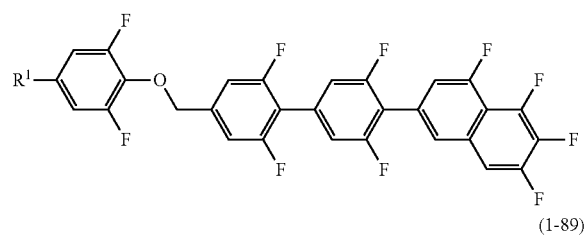
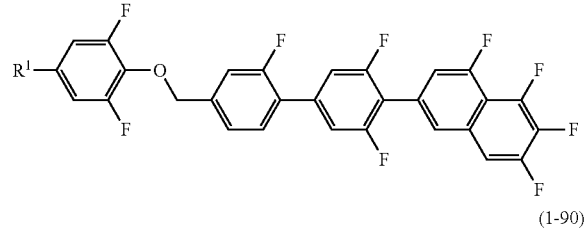
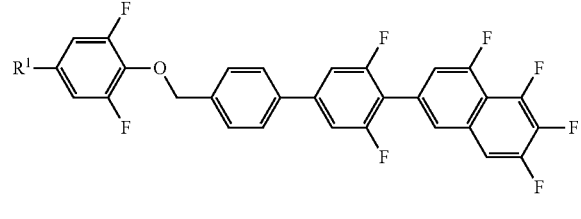
(1-91)
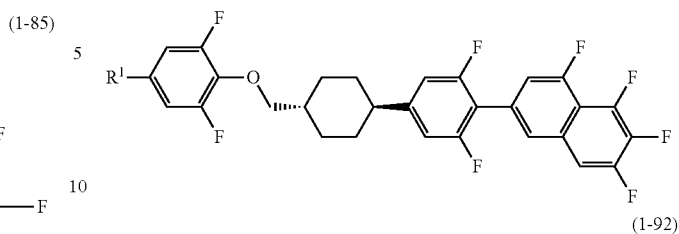
(1-92)
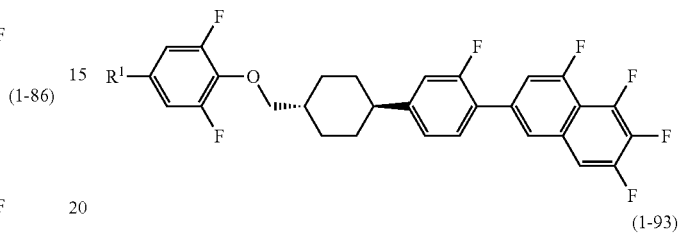
(1-93)
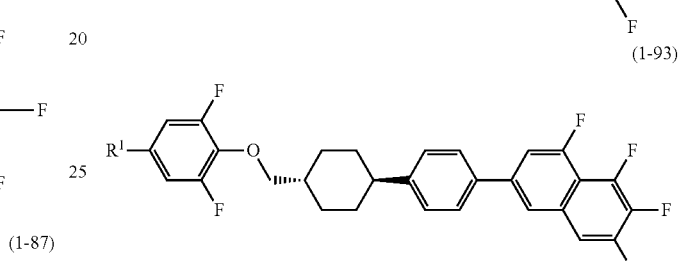
[Chem. 33]
(1-94)
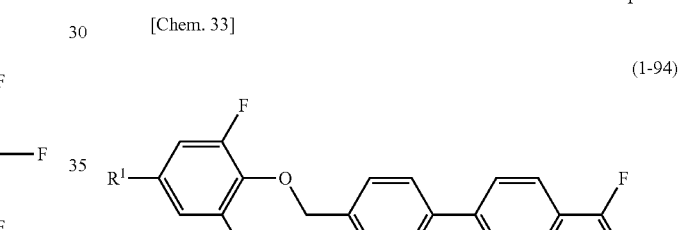
(1-95)
(1-96)
(1-97)
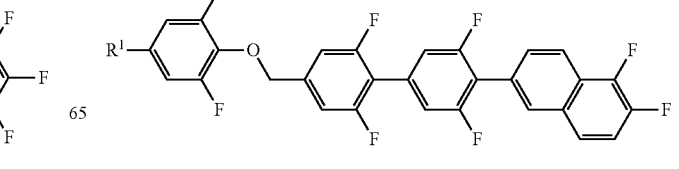
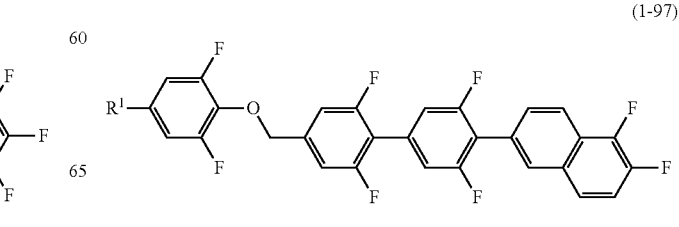

-continued

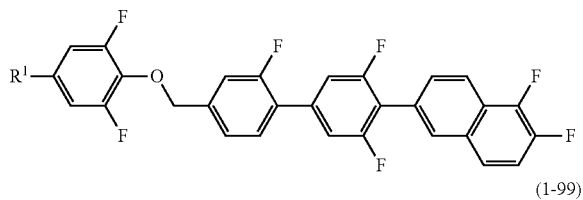
(1-98)

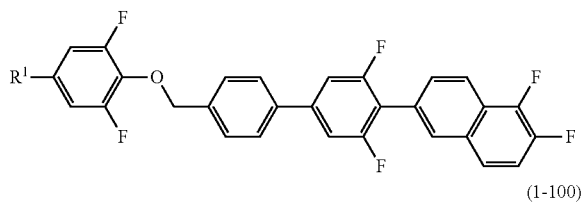
(1-99)

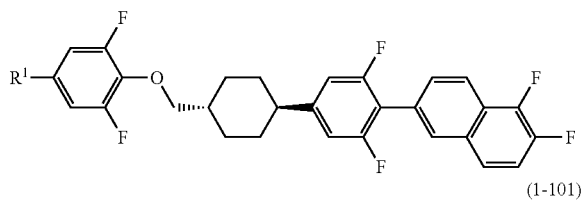
(1-100)

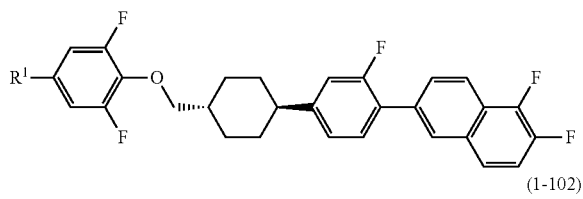
(1-101)

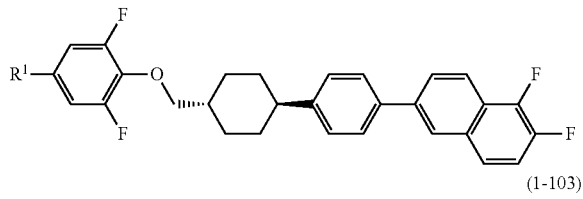
(1-102)

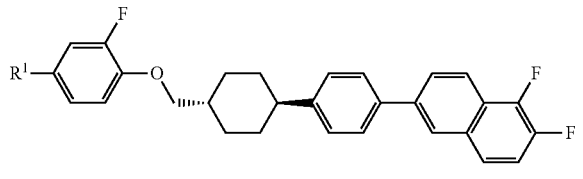
(1-103)

(where each $R^1$ independently represents an alkyl group having 1 to 15 carbon atoms, an alkenyl group having 2 to 15 carbon atoms, an alkoxy group having 1 to 15 carbon atoms, or an alkenyloxy group having 2 to 15 groups).

In the case where the amount of the compound represented by Formula (1) is small in the liquid crystal composition of the present invention, the effects of the compound are not produced; hence, the lower limit of the amount thereof in the liquid crystal composition is preferably 1% ("%" in the composition refers to mass %), more preferably 2%, and further preferably 5%. In the case where the amount of the compound is excessive, a problem such as a precipitation is caused; hence, the upper limit of the amount thereof is preferably 50%, more preferably 30%, further preferably 20%, and especially preferably 10%. The compounds represented by Formula (1) may be used alone or in combination at the same time.

In order to adjust the physical properties of a liquid crystal composition, a compound other than the compound represented by Formula (1) may be used, and a compound which does not exhibit a liquid crystal phase can be optionally added as well as a compound which exhibits a liquid crystal phase.

The composition of the present invention preferably contains a first component that is at least one of the compounds represented by Formula (1) and another component that is at least one of the following second to sixth components which are representative examples of preferred compounds which can be used in combination with the compound represented by Formula (1).

In particular, the second component is a fluorine-based (halogen-based) p-type liquid crystal compound, and examples thereof include compounds represented by Formulae (A1) to (A3).

[Chem. 34]

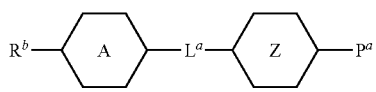
(A1)

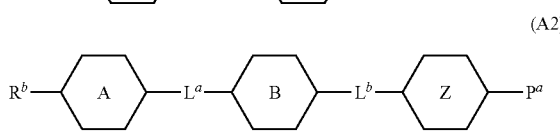
(A2)

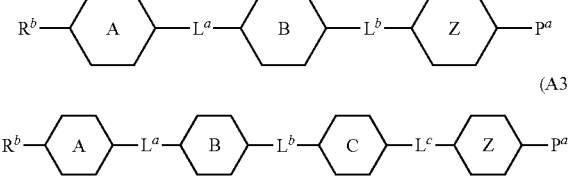
(A3)

In Formulae (A1) to (A3), $R^b$ represents an alkyl group having 1 to 12 carbon atoms which may be linear or branched and which may have a cyclic structure of a 3- to 6-membered ring; in such a group, any —$CH_2$— may be substituted with —O—, —CH=CH—, —CH=CF—, —CF=CH—, —CF=CF—, or —C≡C—, and any hydrogen atom may be substituted with a fluorine atom or a trifluoromethoxy group. $R^b$ is preferably a linear alkyl group having 1 to 7 carbon atoms, a linear 1-alkenyl group having 2 to 7 carbon atoms, a linear 3-alkenyl group having 4 to 7 carbon atoms, or an alkyl group having 1 to 5 carbon atoms and having an end substituted with an alkoxy group having 1 to 3 carbon atoms. In the case where the branched structure has an asymmetric carbon atom, the compound may be an optically active compound or a racemic compound.

Rings A, B, and C each independently represent a trans-1,4-cyclohexylene group, a trans-decahydronaphthalene-trans-2,6-diyl group, a 1,4-phenylene group which may be substituted with at least one fluorine atom, a naphthalene-2,6-diyl group which may be substituted with at least one fluorine atom, a tetrahydronaphthalene-2,6-diyl group which may be substituted with at least one fluorine atom, a 1,4-cyclohexenylene group which may be substituted with a fluorine atom, a 1,3-dioxane-trans-2,5-diyl group, a pyrimidine-2,5-diyl group, or a pyridine-2,5-diyl group; a trans-1,4-cyclohexylene group, a trans-decahydronaphthalene-trans-2,6-diyl group, a naphthalene-2,6-diyl group which may be substituted with a fluorine atom, and a 1,4-phenylene group which may be substituted with one or two fluorine atoms are preferred. In particular, in the case where Ring B is a trans-1,4-cyclohexylene group or a trans-decahydronaphthalene-trans-2,6-diyl group, Ring A is preferably a trans-1,4-cyclohexylene group; in the case where Ring C is a trans-1, 4-cyclohexylene group or a trans-decahydronaphthalene-trans-2,6-diyl group, Rings B and A are each preferably a trans-1,4-cyclohexylene group. In Formula (A3), Ring A is preferably a trans-1,4-cyclohexylene group.

$L^a$, $L^b$, and $L^c$ are each a linking group and independently represent a single bond, an ethylene group (—CH$_2$CH$_2$—), a 1,2-propylene group (—CH(CH$_2$)CH$_2$— and —CH$_2$CH(CH$_2$)—), a 1,4-butylene group, —COO—, —OCO—, —OCF$_2$—, —CF$_2$O—, —CH=CH—, —CH=CF—, —CF=CH—, —CF=CF—, —C≡C—, or —CH=NN=CH—; preferably a single bond, an ethylene group, a 1,4-butylene group, —COO—, —OCF$_2$—, —CF$_2$O—, —CF=CF—, or —C≡C—; and especially preferably a single bond or an ethylene group. In Formula (A2), at least one of $L^a$, $L^b$, and $L^c$ preferably represents a single bond; in Formula (A3), at least two of them each preferably represent a single bond.

Ring Z is an aromatic ring and is represented by any one of the following Formulae (La) to (Lc).

[Chem. 35]

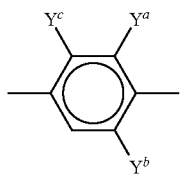

(La)

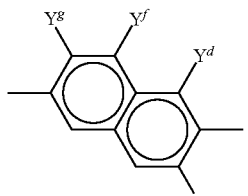

(Lb)

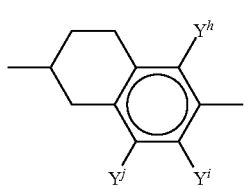

(Lc)

In Formulae (La) to (Lc), $Y^a$ to $Y^j$ each independently represent a hydrogen atom or a fluorine atom. In Formula (La), at least one of $Y^a$ and $Y^b$ is preferably a fluorine atom; in Formula (Lb), at least one of $Y^d$ to $Y^f$ is preferably a fluorine atom, and, in particular, $Y^d$ is further preferably a fluorine atom; and in Formula (Lc), at least one of $Y^h$ and $Y^i$ is preferably a fluorine atom, and, in particular, $Y^h$ is further preferably a fluorine atom.

An end group $P^a$ represents a fluorine atom, a chlorine atom, a trifluoromethoxy group, a difluoromethoxy group, a trifluoromethyl group or difluoromethyl group, an alkoxy group having 2 or 3 carbon atoms and substituted with at least 2 fluorine atoms, an alkyl group having 2 or 3 carbon atoms and substituted with at least 2 fluorine atoms, an alkenyl group having 2 or 3 carbon atoms and substituted with at least 2 fluorine atoms, or an alkenyloxy group having 2 or 3 carbon atoms and substituted with at least 2 fluorine atoms. A fluorine atom, a trifluoromethoxy group, and difluoromethoxy group are preferred, and a fluorine atom is especially preferred.

The third component is a cyano-based p-type liquid crystal compound, and examples thereof include compounds represented by Formulae (B1) to (B3).

[Chem. 36]

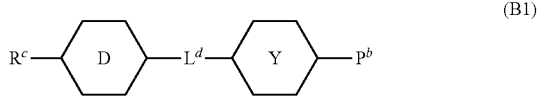

(B1)

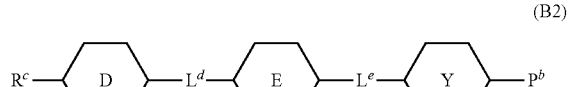

(B2)

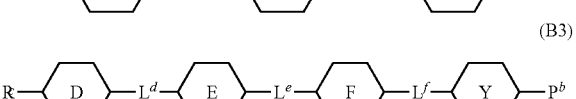

(B3)

In Formulae (B1) to (B3), $R^c$ represents an alkyl group having 1 to 12 carbon atoms which may be linear or branched and which may have a cyclic structure of a 3- to 6-membered ring; in such a group, any —CH$_2$— may be substituted with —O—, —CH=CH—, —CH=CF—, —CF=CH—, —CF=CF—, or —C≡C—, and any hydrogen atom may be substituted with a fluorine atom or a trifluoromethoxy group. $R^c$ is preferably a linear alkyl group having 1 to 7 carbon atoms, a linear 1-alkenyl group having 2 to 7 carbon atoms, a linear 3-alkenyl group having 4 to 7 carbon atoms, or an alkyl group having 1 to 5 carbon atoms and having an end substituted with an alkoxy group having 1 to 3 carbon atoms. In the case where the branched structure has an asymmetric carbon atom, the compound may be an optically active compound or a racemic compound.

Rings D, E, and F each independently represent a trans-1,4-cyclohexylene group, a trans-decahydronaphthalene-trans-2,6-diyl group, a 1,4-phenylene group which may be substituted with at least one fluorine atom, a naphthalene-2,6-diyl group which may be substituted with at least one fluorine atom, a tetrahydronaphthalene-2,6-diyl group which may be substituted with at least one fluorine atom, a 1,4-cyclohexenylene group which may be substituted with a fluorine atom, a 1,3-dioxane-trans-2,5-diyl group, a pyrimidine-2,5-diyl group, or a pyridine-2,5-diyl group; a trans-1,4-cyclohexylene group, a trans-decahydronaphthalene-trans-2,6-diyl group, a naphthalene-2,6-diyl group which may be substituted with a fluorine atom, and a 1,4-phenylene group which may be substituted with one or two fluorine atoms are preferred. In particular, in the case where Ring E is a trans-1,4-cyclohexylene group or a trans-decahydronaphthalene-trans-2,6-diyl group, Ring D is preferably a trans-1,4-cyclohexylene group; in the case where Ring F is a trans-1,4-cyclohexylene group or a trans-decahydronaphthalene-trans-2,6-diyl group, Rings D and E are each preferably a trans-1,4-cyclohexylene group. In Formula (B3), Ring D is preferably a trans-1,4-cyclohexylene group.

$L^d$, $L^e$, and $L^f$ are each a linking group and independently represent a single bond, an ethylene group (—CH$_2$CH$_2$—), a 1,2-propylene group (—CH(CH$_2$)CH$_2$— and —CH$_2$CH(CH$_2$)—), a 1,4-butylene group, —COO—, —OCO—, —OCF$_2$—, —CF$_2$O—, —CH=CH—, —CH=CF—, —CF=CH—, —CF=CF—, —C≡C—, —OCH$_2$—, —CH$_2$O—, or —CH=NN=CH—; preferably a single bond, an ethylene group, —COO—, —OCF$_2$—, —CF$_2$O—, —CF=CF—, or —C≡C—; and especially preferably a single bond, an ethylene group, or —COO—. In Formula (B2), at least one of $L^d$, $L^e$, and $L^f$ preferably represents a single bond; in Formula (B3), at least two of them each preferably represent a single bond.

$P^b$ represents a cyano group.

Ring Y is an aromatic group and is represented by any one of the following Formulae (Ld) to (Lf).

[Chem. 37]

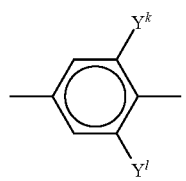
(Ld)

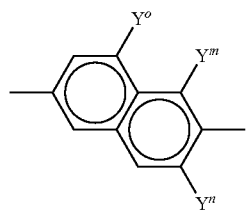
(Le)

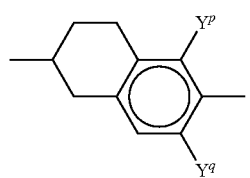
(Lf)

In Formulae (Ld) to (Lf), $Y^k$ to $Y^q$ each independently represent a hydrogen atom or a fluorine atom. In Formula (Ld), at least one of $Y^k$ and $Y^l$ is preferably a fluorine atom; in Formula (Le), at least one of $Y^m$ to $Y^o$ is a fluorine atom, and, in particular, $Y^m$ is further preferably a fluorine atom; and in Formula (Lf), at least one of $Y^p$ and $Y^q$ is preferably a fluorine atom, and, in particular, $Y^p$ is further preferably a fluorine atom.

The fourth component is a non-polar liquid crystal compound having a dielectric anisotropy of approximately zero, and examples thereof include compounds represented by Formulae (C1) to (C3).

[Chem. 38]

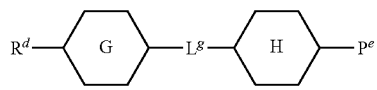
(C1)

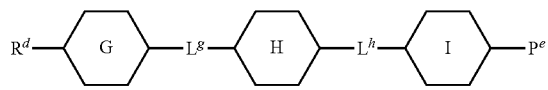
(C2)

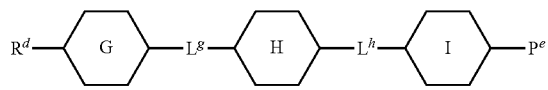
(C3)

In Formulae (C1) to (C3), $R^d$ and $p^e$ each independently represent an alkyl group having 1 to 12 carbon atoms which may be linear or branched and which may have a cyclic structure of a 3- to 6-membered ring; in such a group, any —CH$_2$— may be substituted with —O—, —CH=CH—, —CH=CF—, —CF=CH—, —CF=CF—, or —C≡C—, and any hydrogen atom may be substituted with a fluorine atom or a trifluoromethoxy group. $R^d$ and $P^e$ are each preferably a linear alkyl group having 1 to 7 carbon atoms, a linear 1-alkenyl group having 2 to 7 carbon atoms, a linear 3-alkenyl group having 4 to 7 carbon atoms, a linear alkoxy group having 1 to 3 carbon atoms, or a linear alkyl group having 1 to 5 carbon atoms and having an end substituted with an alkoxy group having 1 to 3 carbon atoms; furthermore, at least one of $R^d$ and $P^e$ is especially preferably a linear alkyl group having 1 to 7 carbon atoms, a linear 1-alkenyl group having 2 to 7 carbon atoms, or a linear 3-alkenyl group having 4 to 7 carbon atoms.

Rings G, H, I, and J each independently represent a trans-1,4-cyclohexylene group, a trans-decahydronaphthalene-trans-2,6-diyl group, a 1,4-phenylene group which may be substituted with one or two fluorine atoms or methyl groups, a naphthalene-2,6-diyl group which may be substituted with at least one fluorine atom, a tetrahydronaphthalene-2,6-diyl group which may be substituted with one or two fluorine atoms, a 1,4-cyclohexenylene group which may be substituted with one or two fluorine atoms, a 1,3-dioxane-trans-2,5-diyl group, a pyrimidine-2,5-diyl group, or a pyridine-2,5-diyl group; each compound preferably contains at most one of a trans-decahydronaphthalene-trans-2,6-diyl group, a naphthalene-2,6-diyl group which may be substituted with at least one fluorine atom, a tetrahydronaphthalene-2,6-diyl group which may be substituted with one or two fluorine atoms, a 1,4-cyclohexenylene group which may be substituted with a fluorine atom, a 1,3-dioxane-trans-2,5-diyl group, a pyrimidine-2,5-diyl group, and a pyridine-2,5-diyl group, and the other rings are preferably a trans-1,4-cyclohexylene group or a 1,4-phenylene group which may be substituted with one or two fluorine atoms or methyl groups. The total number of fluorine atoms contained in Rings G, H, I, and J is preferably not more than two, and more preferably zero or one.

$L^g$, $L^h$, and $L^i$ are each a linking group and independently represent a single bond, an ethylene group (—CH$_2$CH$_2$—), a 1,2-propylene group (—CH(CH$_3$)CH$_2$— and —CH$_2$CH(CH$_3$)—), a 1,4-butylene group, —COO—, —OCO—, —OCF$_2$—, —CF$_2$O—, —CH=CH—, —CH=CF—, —CF=CH—, —CF=CF—, —C≡C—, or —CH=NN=CH—; and preferably a single bond, an ethylene group, a 1,4-butylene group, —COO—, —OCO—, —OCF$_2$—, —CF$_2$O—, —CF=CF—, —C≡C—, or —CH=NN=CH—. In Formula (C2), at least one of $L^g$, $L^h$, and $L^i$ preferably represents a single bond; in Formula (C3), at least two of them each preferably represent a single bond.

Compounds represented by Formulae (C1) to (C3) do not include compounds represented by Formulae (A1) to (A3) and compounds represented by Formulae (B1) to (B3).

The compounds represented by Formulae (A1) to (A3), compounds represented by Formulae (B1) to (B3), and compounds represented by Formulae (C1) to (C3) do not have structures in which hetero atoms are directly connected to each other.

The fifth component is an optically active compound used for inducing a helical structure in a liquid crystal composition. Such a compound is preferably a compound having an asymmetric carbon atom, and more preferably a compound having a 1-methylheptyloxy group.

The sixth component is a compound which has a polymerizable functional group and which can be polymerized by being irradiated with ultraviolet light or by being heated and is added to enhance a response speed or improve molecular orientation in a liquid crystal composition. The polymerizable group is preferably an acryloxy group or a methacryloxy group, and more preferably a methacryloxy group. The number of the polymerizable functional groups is preferably one to three, and more preferably two.

In the present invention, a compound represented by Formula (1) and an ether compound represented by Formula (4) or phenylboronic acid derivative represented by Formula (5), which are intermediates used for efficiently producing the compound represented by Formula (1), can be prepared as follows. Needless to say, the spirit and scope of the present invention are not limited by the following examples of preparation.

(Preparation 1) Method for Preparing Compound Represented by Formula (4) with Dehydrating Condensation Agent A compound represented by Formula (2)

[Chem. 39]

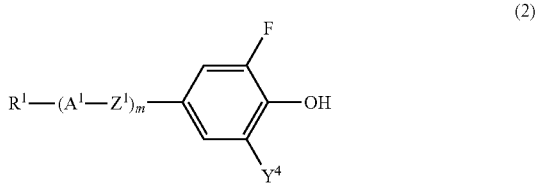

(2)

(where $R^1$, $A^1$, $Z^1$, m, and $Y^4$ each independently represent the same as $R^1$, $A^1$, $Z^1$, m, and $Y^4$ in Formula (1)) is condensed with a compound represented by Formula (3)

[Chem. 40]

$$X^1-CH_2-(A^2-Z^2)_n-A^3-X^2 \qquad (3)$$

(where $X^1$ represents a hydroxyl group, and $A^2$, $A^3$, $Z^2$, n, and $X^2$ each independently represent the same as $A^2$, $A^3$, $Z^2$, n, and $X^2$ in Formula (1)) in the presence of an azodicarboxylic acid and phosphine to prepare a compound represented by Formula (4)

[Chem. 41]

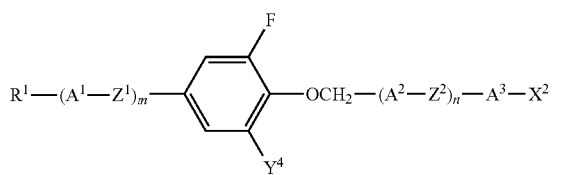

(4)

(where $R^1$, $A^1$, $A^2$, $A^3$, $Z^1$, $Z^2$, m, n, $Y^4$, and $X^2$ each independently represent the same as $R^1$, $A^1$, $A^2$, $A^3$, $Z^1$, $Z^2$, m, n, $Y^4$, and $X^2$ in Formula (2) or (3)).

Although any solvent which allows the reaction to properly proceed can be used, ether solvents such as tetrahydrofuran and diethyl ether are preferably used. Such solvents can be used alone or in combination.

The azodicarboxylic acid is preferably diisopropyl azodicarboxylate or diethyl azodicarboxylate, and more preferably diisopropyl azodicarboxylate.

The phosphine is preferably triphenylphosphine.

In a preferred reaction, the components other than an azodicarboxylate are mixed with each other in advance, and then the azodicarboxylate is finally added thereto; the reaction temperature is not limited provided that the reaction properly proceeds, and the temperature is preferably in the range of −20° C. to 30° C., and more preferably −10° C. to 20° C. After the addition of the azodicarboxylate, the reaction is preferably carried out at room temperature.

(Preparation 2) Method for Preparing Compound Represented by Formula (4) Though Etherification Using Base A compound represented by Formula (2) is allowed to react with a compound represented by Formula (3) in the presence of a base to produce a compound represented by Formula (4).

$X^1$ is preferably a bromine atom, an iodine atom, a tosyloxy group, a mesyloxy group, or a trifluoromethanesulfonyloxy group, and more preferably a bromine atom, an iodine atom, or a trifluoromethanesulfonyloxy group.

Any solvent which allows the reaction to properly proceed can be used; however, the solvent is preferably an ether solvent such as tetrahydrofuran or diethyl ether, an alkylnitrile solvent such as acetonitrile, a ketone solvent such as acetone or methyl ethyl ketone, an aromatic solvent such as benzene or toluene, or an amide solvent such as dimethylformamide or dimethylacetamide, and more preferably tetrahydrofuran, acetonitrile, acetone, methyl ethyl ketone, dimethylformamide, or dimethylacetamide. These solvents may be used alone or in combination.

Any base which allows the reaction to smoothly proceed can be used; however, the base is preferably an alkali metal hydride such as sodium hydride or potassium hydride, an alkali hydroxide such as sodium hydroxide or potassium hydroxide, an alkaline earth metal hydroxide such as barium hydroxide or calcium hydroxide, a carbonate such as potassium carbonate or cesium carbonate, or a tertiary alkylamine such as triethylamine or ethyldiisopropylamine, and more preferably sodium hydride, sodium hydroxide, potassium hydroxide, potassium carbonate, or cesium carbonate. In the case where n is 1 and where $A^2$ is a tetrahydropyranyl group, a dioxane group, or a cyclohexyl group, the base is especially preferably sodium hydride. The bases other than an alkali metal hydride may be used in the form of an aqueous solution.

The reaction may be carried out through any of the following processes:
(a) all of the components and the solvent that are to be used are mixed with each other at room temperature and optionally heated; and
(b) a solution or suspension solution composed of the compound represented by Formula (2) and the base is optionally heated in advance, and a solution of the compound represented by Formula (3) is added thereto. In the process (a), the reaction temperature is not limited provided that the reaction smoothly proceeds; however, a temperature ranging from room temperature to a temperature which enables the reflux of the solvent is preferred. In the process (b), the reaction temperature is not limited provided that the reaction smoothly proceeds; however, a temperature ranging from 0° C. to a temperature which enables the reflux of the solvent is preferred. In particular, in the case where an alkali metal hydride is used as the base, the temperature is preferably in the range of 0° C. to 20° C., and more preferably 0° C. to 10° C. when the compound represented by Formula (3) is added, and a temperature ranging from room temperature to a temperature which enables the reflux of the solvent is preferred after the addition of the compound represented by Formula (3).

(Preparation 3) Method for Preparing Compound Represented by Formula (5) Via Phenyl Grignard Reagent A compound represented by Formula (4) is allowed to react with magnesium metal to produce a phenyl Grignard reagent, the phenyl Grignard reagent is allowed to react with a borate ester, and the resulting product is hydrolyzed and optionally allowed to react with an alcohol or glycol to yield a compound represented by Formula (5)

[Chem. 42]

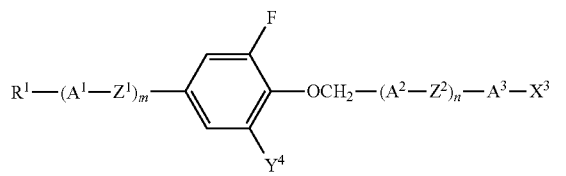

(5)

(where $R^1$, $A^1$, $A^2$, $A^3$, $Z^1$, $Z^2$, m, n, and $Y^4$ each independently represent the same as $R^1$, $A^1$, $A^2$, $A^3$, $Z^1$, $Z^2$, m, n, and $Y^4$ in Formula (1), and $X^3$ represents any of the following

[Chem. 43]

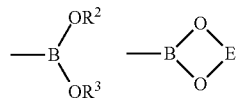

(where $R^2$ and $R^3$ each independently represent an alkyl group which has 1 to 5 carbon atoms and which may be linear or branched,
E represents —$(CH_2)_p$— in which one or more hydrogen atoms may be each independently substituted with a methyl group, and
p is 2, 3, or 4)).

$X^2$ is preferably a chlorine atom, a bromine atom, or an iodine atom, and more preferably a bromine atom.

Any solvent which allows the reaction to smoothly proceed can be used; however, the solvent is preferably an ether solvent, such as tetrahydrofuran, diethyl ether, diisopropyl ether, or tert-butyl methyl ether (tertiary butyl methyl ether), or a hydrocarbon solvent such as hexane or toluene, and more preferably tetrahydrofuran, diethyl ether, or tert-butyl methyl ether. These solvents may be used alone or in combination.

The borate ester is preferably trimethyl borate or triisopropyl borate.

An alcohol or glycol that is optionally used is preferably methanol, ethanol, isopropyl alcohol, ethylene glycol, neopentyl glycol, or 1,1,2,2-tetramethylethylene glycol, and more preferably ethylene glycol or neopentyl glycol.

In the preparation of the phenyl Grignard reagent, the reaction temperature is not limited provided that the reaction smoothly proceeds; however, a temperature ranging from 0° C. to a temperature which enables the reflux of the solvent is preferred, and a temperature ranging from 30° C. to a temperature which enables the reflux of the solvent is more preferred. In the reaction of the obtained phenyl Grignard reagent with the borate ester, the reaction temperature is preferably in the range of −20° C. to 20° C., and more preferably 0° C. to 10° C.

(Preparation 4) Method-1 for Preparing Compound Represented by Formula (5) Via Phenyllithium A compound represented by Formula (4) is allowed to react with an organic metal to produce a phenyllithium, the phenyllithium is allowed to react with a borate ester, and the resulting product is hydrolyzed and optionally allowed to react with an alcohol or glycol, thereby yielding a compound represented by Formula (5).

$X^2$ is preferably a chlorine atom, a bromine atom, or an iodine atom, and more preferably a bromine atom or an iodine atom.

Any solvent which allows the reaction to smoothly proceed can be used; however, the solvent is preferably an ether solvent such as tetrahydrofuran or diethyl ether or a hydrocarbon solvent such as hexane or heptane, and more preferably tetrahydrofuran or diethyl ether. These solvents may be used alone or in combination.

The organic metal is preferably alkylmetal, more preferably alkyllithium; in particular, alkyllithiums such as n-butyllithium (normal butyllithium), sec-butyllithium (secondary butyllithium), and tert-butyllithium (tertiary butyllithium) are preferred, and n-butyllithium is more preferred.

Any borate ester which allows the reaction to smoothly proceed can be used; however, the borate ester is preferably trimethyl borate or triisopropyl borate, more preferably triisopropyl borate.

An alcohol or glycol that is optionally used is preferably methanol, ethanol, isopropyl alcohol, ethylene glycol, neopentylglycol, or 1,1,2,2-tetramethylethylene glycol, and more preferably ethylene glycol or neopentylglycol.

In the preparation of a phenyllithium, the temperature is not limited provided that the reaction smoothly proceeds; however, the temperature is preferably in the range of −78° C. to −30° C., and more preferably −78° C. to −60° C. The temperature is preferably in the range of −78° C. to −40° C. when a borate ester is added after the preparation of the phenyllithium and is preferably slowly increased to 0° C. to 20° C. after the addition of the borate ester.

(Preparation 5) Method-2 for Preparing Compound Represented by Formula (5) Via Phenyllithium A compound represented by Formula (4) in which $X^2$ is a hydrogen atom and in which $A^3$ is a group represented by Formula (A-1) or (A-2) is used to produce a phenyllithium derivative, and then a compound represented by Formula (5) is produced as in (Preparation 4).

The base is preferably an alkyllithium, such as n-butyllithium, s-butyllithium, or tert-butyllithium, or an alkyl lithium amide such as lithium diisopropylamide or lithium dibutyramide, and more preferably butyllithium or lithium diisopropylamide.

Any borate ester which allows the reaction to smoothly proceed can be used; however, the borate ester is preferably trimethyl borate or triisopropyl borate, more preferably triisopropyl borate.

An alcohol or glycol that is optionally used is preferably methanol, ethanol, isopropyl alcohol, ethylene glycol, neopentylglycol, or 1,1,2,2-tetramethylethylene glycol, and more preferably ethylene glycol or neopentylglycol. These solvents may be used alone or in combination.

In the preparation of a phenyllithium derivative, the temperature is not limited provided that the reaction smoothly proceeds; however, the temperature is preferably in the range of −78° C. to −10° C., and more preferably −78° C. to −40° C. The temperature is preferably in the range of −78° C. to −10° C. when a borate ester is added after the preparation of the phenyllithium and is preferably slowly increased to 0° C. to 20° C. after the addition of the borate ester.

(Preparation 6) Method for Preparing Compound Represented by Formula (1) from Compound Represented by Formula (5)

A phenylboronic acid derivative represented by Formula (5) in which $X^3$ is represented by Formula (B-1) or (B-2) is allowed to react with a compound represented by Formula (6)

[Chem. 44]

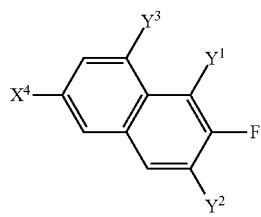

(6)

(where X⁴ represents a trifluoromethanesulfonyloxy group, a chlorine atom, a bromine atom, or an iodine atom, and Y¹, Y², and Y³ each independently represent a hydrogen atom, a fluorine atom, or a chlorine atom) in the presence of a transition metal catalyst and base, thereby yielding a compound represented by Formula (1)

[Chem. 45]

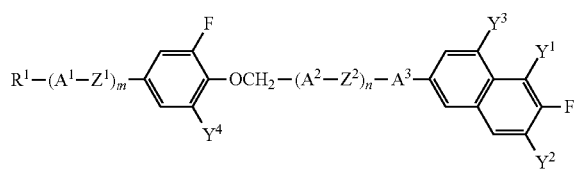

(1)

(where $R^1, A^1, A^2, A^3, Z^1, Z^2, m, n, Y^1, Y^2, Y^3$, and $Y^4$ each independently represent the same as $R^1, A^1, A^2, A^3, Z^1, Z^2, m, n, Y^1, Y^2, Y^3$, and $Y^4$ in Formula (5) or (6)).

Any solvent which allows the reaction to smoothly proceed can be used; however, the solvent is preferably an ether solvent, such as tetrahydrofuran, diethyl ether, or tert-butyl methyl ether, an alcohol solvent such as ethanol, a ketone solvent such as acetone or methyl ethyl ketone, an amide solvent such as N,N-dimethylformamide or N,N-dimethylacetamide, or an aromatic hydrocarbon solvent such as benzene or toluene, and more preferably tetrahydrofuran, ethanol, acetone, methyl ethyl ketone, N,N-dimethylformamide, or toluene. These solvents may be used alone or in combination.

Any transition metal catalyst which allows the reaction to smoothly proceed can be used; however, the transition metal catalyst is preferably a palladium-based transition metal catalyst, such as tetrakis(triphenylphosphine)palladium (0), palladium acetate (II), dichlorobis(triphenylphosphino)palladium (II), or dichloro[1,1'-bis(diphenylphosphino)ferrocene]palladium (II), or a nickel-based transition metal catalyst, and more preferably tetrakis(triphenylphosphine)palladium (0), palladium acetate (II), or dichloro[1,1'-bis(diphenylphosphino)ferrocene]palladium (II). A phosphine ligand may be optionally added to promote the reaction.

Any base which allows the reaction to smoothly proceed can be used; however, the base is preferably an amine reagent such as triethylamine or ethyldiisopropylamine, a carbonate such as potassium carbonate or cesium carbonate, or an alkali metal hydroxide such as sodium hydroxide or potassium hydroxide, and more preferably a carbonate such as potassium carbonate or cesium carbonate. These bases may be optionally in the form of aqueous solutions.

The reaction may be carried out through any of the following processes:

(a) all of the components and solvent that are to be used are mixed with each other in advance and then heated, and (b) a solvent and the components other than a phenylboronic acid derivative represented by Formula (5) are mixed with each other in advance, and then a solution of the phenylboronic acid derivative represented by Formula (5) is added thereto optionally under being heated. In each of the processes (a) and (b), the reaction temperature is preferably in the range of 0° C. to a temperature which enables the reflux of the solvent, and more preferably 40° C. to 110° C.

(Preparation 7) Method-1 for Preparing Compound Represented by Formula (1) from Compound Represented by Formula (4)

An ether compound represented by Formula (4) in which X² is a chlorine atom, a bromine atom, or an iodine atom is allowed to react with magnesium metal to produce a phenyl Grignard reagent represented by Formula (5) in which X³ is MgX⁴, and then the phenyl Grignard reagent is allowed to react with a compound represented by Formula (6) in the presence of a transition metal catalyst to yield a compound represented by Formula (1).

Any solvent which allows the reaction to smoothly proceed can be used; however, the solvent is preferably an ether solvent, such as tetrahydrofuran, diethyl ether, or tert-butyl methyl ether, or an aromatic hydrocarbon solvent such as benzene, toluene, or xylene, and more preferably tetrahydrofuran, tert-butyl methyl ether, toluene, or xylene. These solvents may be used alone or in combination.

Any transition metal catalyst which allows the reaction to smoothly proceed can be used; however, the transition metal catalyst is preferably a palladium-based transition metal catalyst, such as tetrakis(triphenylphosphine)palladium (0), palladium acetate (II), dichlorobis(triphenylphosphino)palladium (II), or dichloro[1,1'-bis(diphenylphosphino)ferrocene] palladium (II), or a nickel-based transition metal catalyst, and more preferably tetrakis(triphenylphosphine)palladium (0), palladium acetate (II), or dichloro[1,1'-bis(diphenylphosphino)ferrocene]palladium (II). A phosphine ligand may be added to promote the reaction.

The reaction temperature is not limited provided that the reaction smoothly proceeds; however, the temperature is preferably in the range of 0° C. to a temperature which enables the reflux of the solvent, and more preferably 60° C. to 110° C.

(Preparation 8) Method-2 for Preparing Compound Represented by Formula (1) from Compound Represented by Formula (4)

An ether compound represented by Formula (4) in which X² is a chlorine atom, a bromine atom, or an iodine atom is allowed to react with an alkylmetal to produce a phenyllithium represented by Formula (5) in which X³ is Li. The produced compound is directly used or optionally subjected to transmetallation to change the metal species. Then, the resulting compound is allowed to react with a fluorinated naphthalene derivative represented by Formula (6) in the presence of a transition metal catalyst to yield a compound represented by Formula (1).

Any solvent which allows the reaction to smoothly proceed can be used; however, the solvent is preferably an ether solvent, such as tetrahydrofuran, diethyl ether, or tert-butyl methyl ether, a hydrocarbon solvent such as hexane or heptane, or an aromatic hydrocarbon solvent such as toluene or xylene, and more preferably tetrahydrofuran or tert-butyl methyl ether. These solvents may be used alone or in combination.

Any transition metal catalyst which allows the reaction to smoothly proceed can be used; however, the transition metal catalyst is preferably a palladium-based transition metal catalyst, such as tetrakis(triphenylphosphine)palladium (0), palladium acetate (II), dichlorobis(triphenylphosphino)palladium (II), or dichloro[1,1'-bis(diphenylphosphino)ferrocene]palladium (II), or a nickel-based transition metal catalyst, and more preferably tetrakis(triphenylphosphine)palladium (0), palladium acetate (II), or dichloro[1,1'-bis(diphenylphosphino)ferrocene]palladium (II). A phosphine ligand may be added to promote the reaction.

An alkyllithium reagent is preferably n-butyllithium, sec-butyllithium, or tert-butyllithium, and more preferably n-butyllithium.

A metal salt is used in the transmetallation that is optionally carried out and preferably zinc chloride or magnesium chloride. Use of zinc chloride enables production of a compound represented by Formula (5) in which $X^3$ is ZnCl, and use of magnesium chloride enables production of a compound represented by Formula (5) in which $X^3$ is MgCl.

The reaction temperature is not limited provided that the reaction smoothly proceeds; however, the reaction temperature is preferably in the range of −76° C. to −40° C., and more preferably −76° C. to −60° C.

(Preparation 9) Method-3 for Preparing Compound Represented by Formula (1) from Compound Represented by Formula (4)

A compound represented by Formula (4) in which $X^2$ is a hydrogen atom and in which $A^3$ is represented by Formula (A-1) or (A-2) is allowed to react with a base to produce a phenyllithium. The phenyllithium is directly used or optionally subjected to transmetallation to change the metal species. Then, the resulting compound is allowed to react with a compound represented by Formula (6) in the presence of a transition metal catalyst to yield a compound represented by Formula (1).

Any solvent which allows the reaction to smoothly proceed can be used; however, the solvent is preferably an ether solvent, such as tetrahydrofuran, diethyl ether, or tert-butyl methyl ether, a hydrocarbon solvent such as hexane or heptane, or an aromatic hydrocarbon solvent such as toluene or xylene, and more preferably tetrahydrofuran or tert-butyl methyl ether. These solvents may be used alone or in combination.

Any transition metal catalyst which allows the reaction to smoothly proceed can be used; however, the transition metal catalyst is preferably a palladium-based transition metal catalyst, such as tetrakis(triphenylphosphine)palladium (0), palladium acetate (II), dichlorobis(triphenylphosphino)palladium (II), or dichloro[1,1'-bis(diphenylphosphino)ferrocene]palladium (II), or a nickel-based transition metal catalyst, and more preferably tetrakis(triphenylphosphine)palladium (0), palladium acetate (II), or dichloro[1,1'-bis(diphenylphosphino)ferrocene]palladium (II). A phosphine ligand may be added to promote the reaction.

The base is preferably an alkyllithium reagent, such as n-butyllithium, sec-butyllithium, or tert-butyllithium, or lithium diisopropylamide, and more preferably n-butyllithium or lithium diisopropylamide.

A metal salt is used in the transmetallation that is optionally carried out and preferably zinc chloride or magnesium chloride.

The reaction temperature is not limited provided that the reaction smoothly proceeds; however, the reaction temperature is preferably in the range of −76° C. to −40° C., and more preferably −76° C. to −60° C. in the case where an alkyllithium is used as the base and is preferably in the range of −76° C. to −10° C., and more preferably −40° C. to −20° C. in the case where a lithium amide is used as the base.

EXAMPLES

The present invention will now be described further in detail with reference to Examples but is not limited thereto.

Phase transition temperature was measured with both a polarizing microscope having a temperature-controlled stage and a differential scanning calorimeter (DSC).

In compositions of Examples and Comparative Examples, the term "%" is on a mass basis.

The term "$T_n$," refers to temperature of transition between a nematic phase and an isotropic phase.

Compounds are abbreviated as follows.

THF: tetrahydrofuran

DMF: N,N-dimethylformamide

DIAD: diisopropyl azodicarboxylate

TPP: triphenylphosphine

Me: methyl group, Pr: n-propyl group, Bu: n-butyl group

Tf: trifluoromethanesulfonyl group

LDA: lithium diisopropylamide

Example 1

Production of [4-(5,6,7-trifluoronaphthalene-2-yl)phenyl]-(2,6-difluoro-4-propylphenyloxy)methane

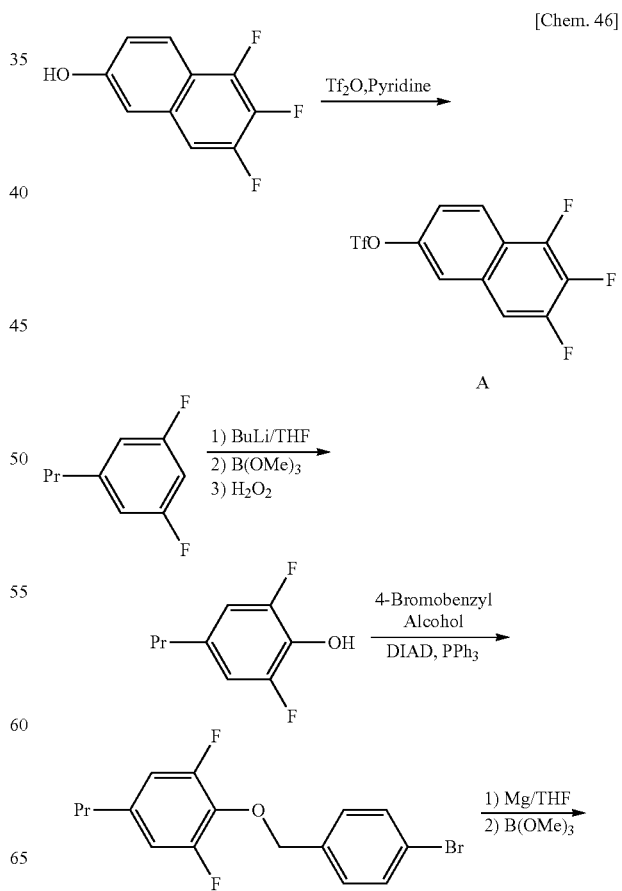

[Chem. 46]

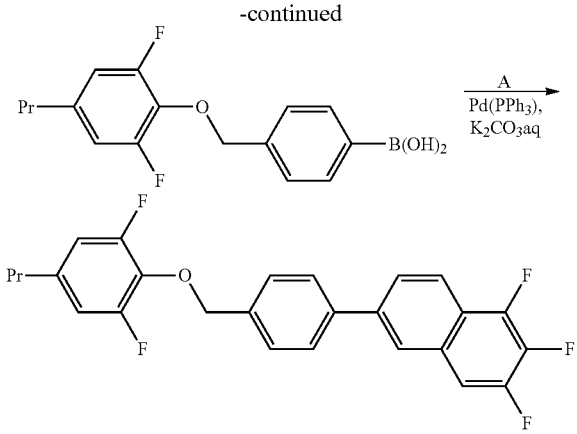

(1-1) Under a nitrogen atmosphere, 5,6,7-trifluoro-2-naphthol (208 g, prepared as disclosed in Japanese Unexamined Patent Application Publication No. 2004-91361) and pyridine (125 g) were dissolved in dichloromethane (1000 mL), and the product was cooled with ice. A solution in which a trifluoromethanesulfonic anhydride (310 g) had been dissolved in dichloromethane (620 mL) was added thereto at a rate that did not allow the internal temperature to exceed 15° C., and the product was stirred at room temperature for 7 hours. Under cooling with ice, 15% hydrochloric acid (700 mL) was added to the product to separate the organic layer. The organic layer was washed with saturated aqueous sodium hydrogen carbonate and a saturated salt solution in sequence, sodium sulfate was added thereto for dehydration. The solvent was distilled off under reduced pressure, and the product was purified by silica gel column chromatography, thereby yielding a transparent liquid that was trifluoromethanesulfonic acid=5,6,7-trifluoronaphthalene-2-yl ester (297 g, A).

(1-2) Under a nitrogen atmosphere, 3,5-difluoropropylbenzene (134 g, synthesized as disclosed in *Molecular Crystals and Liquid Crystals,* 1995, 260, 93-106) was dissolved in THF (650 mL) and then cooled to −40° C. or lower. Then, 1.6 mol/L of an n-butyllithium/hexane solution (640 mL) was added thereto at a rate which did not allow the internal temperature to be −35° C. or higher, and the product was further stirred for an hour at −40° C. Then, a solution in which trimethyl borate (116 g) had been dissolved in THF (350 mL) at −40° C. was added thereto at a rate which did not allow the internal temperature to be −35° C. or higher. The temperature was slowly increased to room temperature, the product was further stirred for 30 minutes at room temperature, 10% hydrochloric acid (400 mL) was subsequently added thereto under cooling with ice to separate the organic layer, and the organic layer was washed with a saturated salt solution. Then, 15% hydrogen peroxide solution (215 g) was slowly added thereto, and then the product was stirred for 6 hours while being heated to 40° C. The product was cooled with ice, and an aqueous solution of 20% sodium sulfite (300 mL) was added thereto at a rate which did not allow the internal temperature to exceed 20° C. to separate the organic layer. Ethyl acetate (500 mL) was added to the water layer for extraction, the organic layer was added thereto and then washed with a saturated salt solution, and sodium sulfate was added thereto for dehydration. The solvent was distilled off under reduced pressure, hexane (800 mL) was added to the product, and an insoluble matter was removed by filtration. Then, the filtrate was concentrated under reduced pressure to yield a yellow liquid that was 4-propyl-2,6-difluorophenol (123 g).

MS m/z: 172 [M+]
¹HNMR (CDCl₃, TMS internal standard substance) δ (ppm)=6.86 (2H, d, J=8.4 Hz), 2.49 (2H, t, J=7.2 Hz), 1.59 (2H, quinted, j=7.4 Hz), 0.92 (3H, t, J=7.3 Hz)

(1-3) Into THF (300 mL), 2,6-difluoro-4-propylphenol (50 g), 4-bromobenzyl alcohol (54.2 g), and triphenylphosphine (83.7 g) were dissolved, and the product was cooled to −10° C. Then, DIAD (61.7 g) was added thereto at a rate which did not allow the internal temperature to be 5° C. or higher, and the product was subsequently stirred for 3 hours at room temperature. Water (5 mL) was added to the product, the solvent was subsequently distilled off under reduced pressure, then hexane (600 mL) and 70% tert-butyl hydroperoxide (10 g) were added thereto, and the product was stirred for 2 hours at room temperature. The precipitate was removed by filtration, an aqueous solution of 65% methanol (600 mL) was added to the filtrate for separation, and the organic layer was separated. The organic layer was washed with an aqueous solution of 65% methanol (500 mL) and unsaturated salt solution (500 mL) in sequence. Then, sodium sulfate was added to the product for dehydration, the solvent was distilled off, and the product was purified by silica gel column chromatography, thereby yielding a yellow liquid that was 4-[(2,6-difluoro-4-propylphenyloxy)methyl]bromobenzene (83.6 g).

MS m/z: 340, 342 [M+]
¹HNMR (CDCl₃, TMS internal standard substance) δ (ppm)=7.47 (2H, d, J=8.2 Hz), 7.31 (2H, d, J=8.4 Hz), 6.68 (4H, d, j=9.0 Hz), 5.05 (2H, s), 2.48 (2H, t, J=7.3 Hz), 1.59 (2H, quinted, j=7.5 Hz), 0.91 (3H, t, J=7.2 Hz)

(1-4) Under a nitrogen atmosphere, a solution in which 4-(2,6-difluoro-4-propylphenyloxymetyl)bromobenzene (83.6 g) had been dissolved in THF (120 mL) was dropped into a suspension solution of 6.3 g of magnesium and 20 mL of THF at a rate which allowed moderate reflux. After the dropping, the product was stirred for 3 hours at 65° C. and then cooled with ice. A solution in which trimethyl borate (28.0 g) had been dissolved in THF (100 mL) was added to the product at a rate which did not allow the internal temperature to be 10° C. or higher, and the product was stirred for 2 hours at room temperature. Then, 10% hydrochloric acid was added thereto until the inside of the system entered an acid state, and the product was stirred for 30 minutes. The organic layer was separated, toluene was added to the water layer for extraction, the organic layer was added thereto, and the organic layer was washed with a saturated salt solution. Sodium sulfate was added thereto for dehydration, and the solvent was distilled off under reduced pressure, thereby yielding a yellow liquid that was 4-[(2,6-difluoro-4-propylphenyloxy)methyl]phenylboric acid (64.0 g).

¹HNMR (CDCl₃, TMS internal standard substance) δ (ppm)=7.58 (2H, d, J=7.7 Hz), 7.48 (2H, d, J=8.3 Hz), 6.70 (2H, d, j=7.4 Hz), 5.11 (2H, s), 2.49 (2H, t, J=7.3 Hz), 1.59 (2H, quinted, j=7.5 Hz), 0.92 (3H, t, J=7.2 Hz)

(1-5) Under a nitrogen atmosphere, a solution in which 4-[(2,6-difluoro-4-propylphenyloxy)methyl]phenylboric acid (8.0 g), the product A obtained in (1-1) (7.8 g), tetrakis(triphenylphosphine)palladium (0) (0.55 g), an aqueous solution of 2M potassium carbonate (18 mL), and 40 mL of THF had been mixed with each other was stirred for 4 hours at 60° C. The product was left to stand for cooling, water and toluene were subsequently added thereto for separation, the organic layer was washed with a saturated salt solution, sodium sulfate was added thereto for dehydration, and the solvent was distilled off under reduced pressure. The product was purified by silica gel column chromatography, and the purified product was recrystallized from ethanol, thereby yielding a white solid that was [4-(5,6,7-trifluoronaphthalene-2-yl)phenyl]-(2,6-difluoro-4-propylphenyloxy)methane (2.8 g).

MS m/z: 442 [M+]

Phase transition temperature (° C.): Cr 57.8 N 67.3 Iso $^1$HNMR (CDCl$_3$, TMS internal standard substance) δ (ppm)=8.05 (1H, d, J=8.7 Hz), 7.88 (1H, s), 7.75 (1H, d, j=8.7 Hz), 7.65 (2H, d, j=8.0 Hz), 7.56 (2H, d, j=8.0 Hz), 7.40-7.35 (1H, m), 6.70 (2H, d, j=8.5 Hz), 5.17 (2H, s), 2.49 (2H, t, 7.7 Hz), 1.59 (2H, quinted quintet, j=7.4 Hz), 0.92 (3H, t, j=7.4 Hz)

Example 2

Production of [3,5-difluoro-4-(5,6,7-trifluoronaphthalene-2-yl)phenyl]-(2,6-difluoro-4-propylphenyloxy)methane

[Chem. 47]

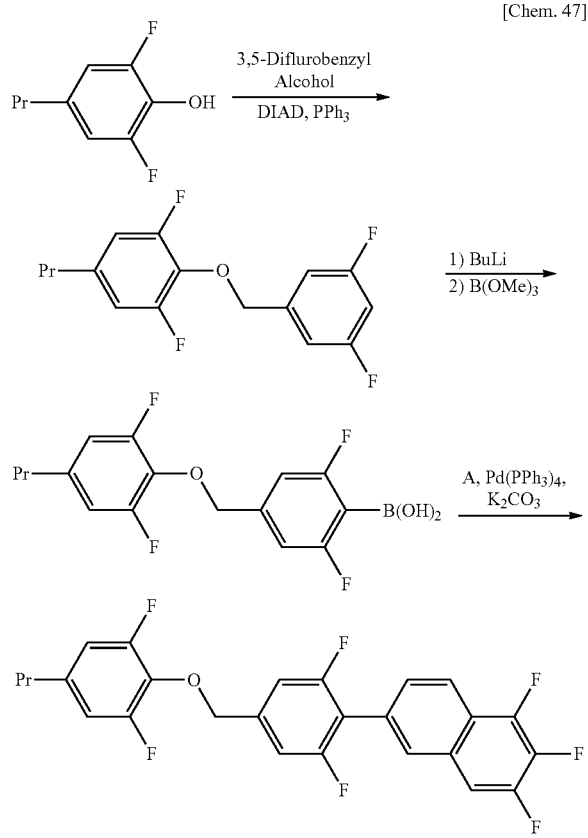

(2-1) Into THF (85 mL), 2,6-difluoro-4-propylphenol obtained in (1-2) in Example 1 (17.2 g), 3,5-difluorobenzyl alcohol (17.2 g), triphenylphosphine (28.9 g) were dissolved, and the product was cooled to −10° C. DIAD (21.2 g) was added thereto at a rate which did not allow the internal temperature to exceed 15° C., and the product was stirred for 3 hours at room temperature. Then, 5 mL of water was added thereto, the solvent was distilled off under reduced pressure, hexane (300 mL) was added thereto, and the product was stirred. The precipitate was removed by filtration, the filtrate was washed with an aqueous solution of 50% methanol (200 mL) and a saturated salt solution in sequence, and sodium sulfate was added thereto for dehydration. The solvent was distilled off under reduced pressure, and the product was purified by silica gel column chromatography, thereby yielding a slightly yellow liquid that what 1,3-difluoro-5-[(2,6-difluoro-4-propylphenyloxy)methyl]benzene (19.1 g).

MS m/z: 298 [M+]

$^1$HNMR (CDCl$_3$, TMS internal standard substance) δ (ppm)=6.99 (2H, d, J=6.2 Hz), 6.78-6.68 (3H, m), 5.08 (2H, s), 2.50 (2H, t, J=7.2 Hz), 1.60 (2H, quinted, j=7.4 Hz), 0.92 (3H, t, J=7.3 Hz)

(2-2) Into THF (50 mL), 1,3-difluoro-5-[(2,6-difluoro-4-propylphenyloxy)methyl]benzene (10.0 g) was dissolved, and the product was cooled to −70° C. To the product, 1.6 mol/L of an n-butyllithium/hexane solution (23 mL) was added at a rate which did not allow the internal temperature to be −60° C. or higher, and then the product was stirred for 30 minutes at −70° C. Then, a solution in which trimethyl borate (4.2 g) had been dissolved in THF (20 mL) was added to the product at a rate which did not allow the internal temperature to exceed −60° C., the temperature was slowly increased to room temperature, and the product was stirred for 30 minutes at room temperature. The product was cooled with ice, 10% hydrochloric acid and toluene were added thereto to separate the organic layer, and toluene was added to the water layer for extraction. The organic layer was added thereto and washed with a saturated salt solution, and sodium sulfate was added thereto for dehydration. The solvent was distilled off under reduced pressure, thereby yielding a clear yellow solid that was 2,6-difluoro-4-[(2,6-difluoro-4-propylphenyloxy)methyl]phenylboric acid (11.4 g).

$^1$HNMR (CDCl$_3$, TMS internal standard substance) δ (ppm)=6.95 (2H, d, J=6.8 Hz), 6.71 (2H, d, j=8.7 Hz), 5.07 (2H, s), 2.50 (2H, t, J=7.4 Hz), 1.61 (2H, quinted, j=7.4 Hz), 0.93 (3H, t, J=7.4 Hz)

(2-3) Under a nitrogen atmosphere, 2,6-difluoro-4-[(2,6-difluoro-4-propylphenyloxy)methyl]phenylboric acid (10.0 g), the product A obtained in (1-1) in Example 1 (8.0 g), anhydrous potassium carbonate (5.0 g), and tetrakis(triphenylphosphine)palladium (0) (0.56 g) were dissolved in acetone (40 mL), and the solution was stirred for 6 hours while being heating to reflux. The product was left to stand for cooling, then water and toluene were added thereto to separate the organic layer, toluene was added to the water layer for extraction, the organic layer was added thereto and washed with a saturated salt solution, and sodium sulfate was added thereto for dehydration. The solvent was distilled off under reduced pressure, the product was purified by silica gel column chromatography, and the purified product was recrystallized from a mixed solvent of ethanol and acetone, thereby yielding a white solid that was [3,5-difluoro-4-(5,6,7-trifluoronaphthalene-2-yl)phenyl]-(2,6-difluoro-4-propylphenyloxy)methane (2.3 g).

MS m/z: 478 [M+]

Phase transition temperature (° C.): Cr 128 Iso $^1$HNMR (CDCl$_3$, TMS internal standard substance) δ (ppm)=8.11 (1H, d, J=8.7 Hz), 7.87 (1H, s), 7.62 (1H, d, j=8.64 Hz), 7.45-7.40 (1H, m), 7.14 (2H, d, J=7.9 Hz), 6.74 (2H, d, j=9.0 Hz), 5.14 (1H, s), 2.52 (2H, t, J=7.3 Hz), 1.61 (2H, quinted, j=7.5 Hz), 0.93 (3H, t, J=7.3 Hz)

Example 3

Production of [trans-4-(4-(5,6,7-trifluoronaphthalene-2-yl)-3,5-difluorophenyl)cyclohexyl)-(2,6-difluoro-4-propylphenyloxy)]methane

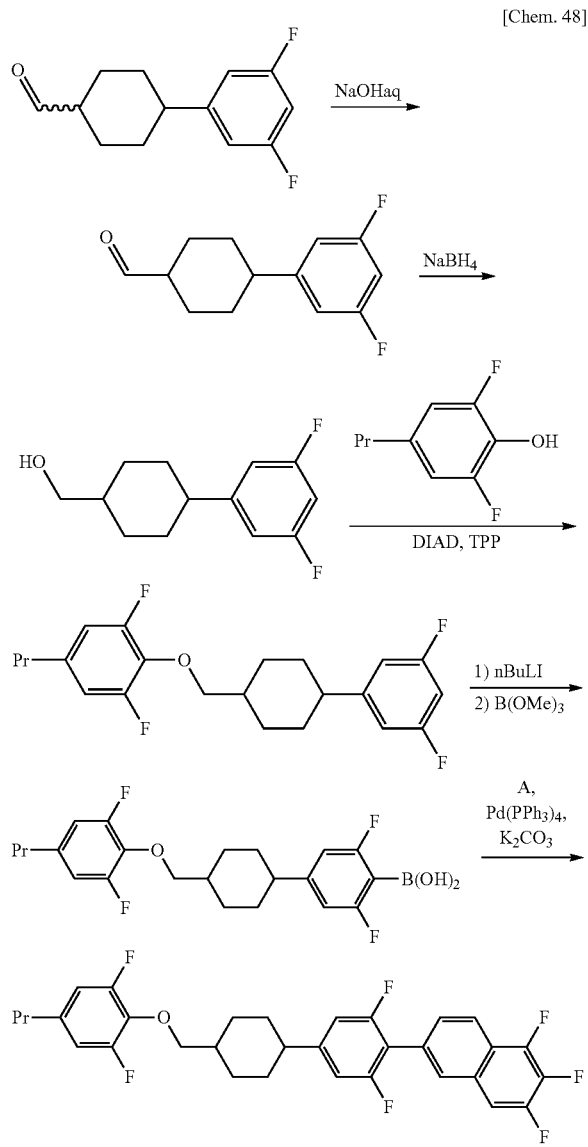

[Chem. 48]

(3-1) Into methanol (360 mL), 4-(3,5-difluorophenyl)cyclohexanecarbaldehyde (120 g, synthesized as disclosed in Japanese Unexamined Patent Application Publication No. 2009-132927) was dissolved, the solution was cooled to −20° C., 20 mL of an aqueous solution of 10% sodium hydroxide was added thereto, and the product was further stirred for an hour at −20° C. To the product, 10% hydrochloric acid was added for neutralization, water (300 mL), THF (200 mL), and ethyl acetate (400 mL) were added, and the organic layer was washed twice with a saturated salt solution and then dehydrated with anhydrous sodium sulfate. The solvent was distilled off under reduced pressure, thereby yielding a pale yellow liquid that was trans-4-(3,5-difluorophenyl)cyclohexanecarbaldehyde (112 g).

(3-2) Trans-4-(3,5-difluorophenyl)cyclohexanecarbaldehyde (112 g) was dissolved in ethanol (224 mL), THF (30 mL), and water (30 mL), sodium boron hydride (9.4 g) was slowly added thereto at an external temperature of 5° C., and the product was stirred for 10 minutes at an external temperature of 5° C. The reaction solution was slowly added to 10% hydrochloric acid (450 mL), and the product was stirred for 30 minutes. Then, the organic layer was separated, the water layer was extracted with ethyl acetate, and the organic layer was added thereto and washed twice with a saturated salt solution. The product was dehydrated with anhydrous sodium sulfate, and then the solvent was distilled off under reduced pressure, thereby yielding a pale yellow liquid that was [trans-4-(3,5-difluorophenyl)cyclohexyl]methanol (110 g).

(3-3) Under a nitrogen atmosphere, 2,6-difluoro-4-propylphenol obtained in (1-2) in Example 1 (70 g), [trans-4-(3,5-difluorophenyl)cyclohexyl]methanol (83 g), and triphenylphosphine (110 g) were dissolved in THF (400 mL), and then DIAD (81.2 g) was dropped thereto at an internal temperature of not more than 23° C. The product was stirred for two hours at room temperature, water (10 mL) was added thereto, and the solvent was distilled off under reduced pressure. Hexane (200 mL), water (20 mL), and methanol (300 mL) were added to the residue to separate the organic layer, the water layer was extracted with hexane and then added to the organic layer, and the product was washed with an aqueous solution of 50% methanol twice and with a saturated salt solution in sequence. The resulting solution was purified by silica gel column chromatography, and the purified product was recrystallized from ethanol, thereby yielding a colorless solid that was trans-4-(3,5-difluorophenyl)cyclohexyl)-(2,6-difluoro-4-propylphenyloxy)methane (80 g).

(3-4) Under a nitrogen atmosphere, trans-4-(3,5-difluorophenyl)cyclohexyl)-(2,6-difluoro-4-propylphenyloxy)methane (40 g) was dissolved in THF (400 mL), the solution was cooled to −60° C., 1.6 mol/L of an n-butyllithium/hexane solution (70 mL) was added thereto at a rate which did not allow the internal temperature to be −40° C. or higher, and the product was further stirred for an hour at −60° C. Then, a solution in which trimethyl borate (13 g) had been dissolved in THF (50 mL) was dropped thereto at a rate which did not allow the internal temperature to be −40° C. or higher. The internal temperature was increased to 0° C., 10% hydrochloric acid was added thereto to make the product acidic, and then the organic layer was separated. Ethyl acetate was added to the water layer for extraction, the organic layer was added thereto and then washed twice with a saturated salt solution, and the product was dehydrated with anhydrous sodium sulfate. The solvent was distilled off under reduced pressure to yield a pale yellow solid that was 2,6-difluoro-4-[trans-4-(2,6-difluoro-4-propylphenyloxymethyl)cyclohexyl]phenylboric acid (44 g).

(3-5) Under a nitrogen atmosphere, 2,6-difluoro-4-[trans-4-(2,6-difluoro-4-propylphenyloxymethyl)cyclohexyl]phenylboric acid (15 g), the product A obtained in (1-1) in Example 1 (11.6 g), anhydrous potassium carbonate (7.3 g), and tetrakis(triphenylphosphine)palladium (0) (0.82 g) were dissolved in acetone (60 mL), and the solution was stirred for 8 hours while being heated to reflux. The product was left to stand for cooling, water and toluene were added to the product to separate the organic layer, toluene was added to the water layer for extraction, the organic layer was added thereto and washed with a saturated salt solution, and sodium sulfate was added thereto for dehydration. The solvent was distilled off under reduced pressure, the product was purified by silica gel column chromatography, and the purified product was recrystallized from a mixed solvent of ethanol and acetone, thereby yielding a white solid that was trans-4-(4-(5,6,7-trifluoronaphthalene-2-yl)-3,5-difluorophenyl)cyclohexyl)-(2,6-difluoro-4-propylphenyloxy)methane (13.3 g).

MS m/z: 560 [M+]

Phase transition temperature (° C.): Cr 125 N 192 Iso $^1$HNMR(CDCl$_3$, TMS internal standard substance) δ (ppm)=8.10 (1H, d, J=8.80 Hz), 7.87 (1H, s), 7.63 (1H, d, =8.72 Hz), 7.43-7.39 (1H, m), 6.90 (2H, d, J=8.88 Hz), 6.71 (2H, d, J=8.96 Hz), 3.95 (2H, d, J=6.28 Hz), 2.61-2.49 (3H, m), 2.12-2.01 (4H, m), 1.91-1.81 (1H, m), 1.65-1.46 (4H, m), 1.33-1.22 (2H, m), 0.93 (3H, t, J=7.44 Hz)

Example 4

Production of [4-(3,5-difluoro-4-(5,6,7-trifluoronaphthalene-2-yl)phenyl)phenyl]-(2,6-difluoro-4-propylphenyloxy)methane

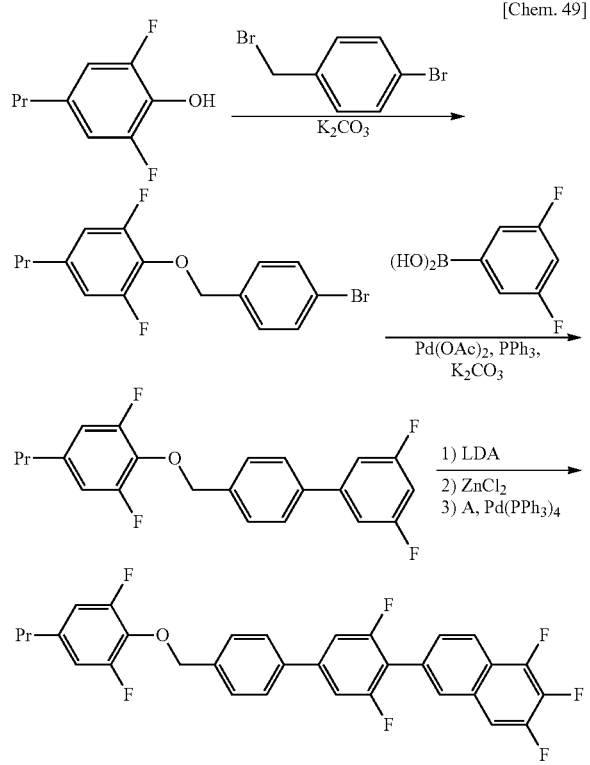

[Chem. 49]

(4-1) Under a nitrogen atmosphere, a suspension solution in which 4-propyl-2,6-difluorophenol obtained in (1-2) in Example 1 (31 g), 4-bromobenzyl bromide (45 g), and potassium carbonate (37.3 g) had been mixed with DMF (180 mL) was heated to 60° C. and then stirred for 6 hours. The product was left to stand for cooling to room temperature, water (200 mL) and hexane (300 mL) were added to the product to separate the organic layer, and hexane (300 mL) was added to the water layer for extraction. The organic layer was added thereto and washed three times with a saturated salt solution (300 mL), and sodium sulfate was added thereto for dehydration. The solvent was distilled off under reduced pressure, and the product was purified by silica gel column chromatography, thereby yielding a colorless transparent liquid that was 4-[(2,6-difluoro-4-propylphenyloxy)methyl]bromobenzene (48.1 g).

(4-2) Under a nitrogen atmosphere, 4-[(2,6-difluoro-4-propylphenyloxy)methyl]bromobenzene (48.1 g), palladium acetate (II) (1.6 g), and triphenylphosphine (3.7 g) were dissolved in ethanol (480 mL), and the solution was heated to 60° C. A solution in which 3,5-difluorophenylboronic acid (26.7 g) had been dissolved in ethanol (80 mL) was slowly added thereto, and the product was further stirred for 5 hours at 60° C. The reaction solution was left to stand for cooling to room temperature, and water (1 L) and toluene (400 mL) were added to the reaction solution to separate the organic layer. The organic layer was washed tree times with a saturated salt solution, and the sodium sulfate was added thereto for dehydration. The solvent was distilled off under reduced pressure, the product was purified by silica gel column chromatography, and the purified product was recrystallized from a mixed solvent of ethanol and acetone, thereby yielding a white solid that was [4-(3,5-difluorophenyl)phenyl]-(3,5-difluoro-4-propylphenyl)methane (40.6 g).

MS m/z: 374[M+]

(4-3) Under a nitrogen atmosphere, diisopropylamine (14.3 g) was dissolved in THF (140 mL), and the solution was cooled to −40° C. Then, 1.6 mol/L of an n-butyllithium/hexane solution (75 mL) was added to the product at a rate which did not allow the internal temperature to be −35° C. or higher, and the product was further stirred for 30 minutes at −40° C. A solution in which [4-(3,5-difluorophenyl)phenyl]-(3,5-difluoro-4-propylphenyl)methane (40.6 g) had been dissolved in THF (200 mL) was added to the product at a rate which did not allow the internal temperature to be −35 or higher, and the product was further stirred for an hour at −40° C. Zinc chloride (17.7 g) was slowly added thereto at a rate which did not allow the internal temperature to be −35° C. or higher, the product was further stirred for 30 minutes at −40° C., and the temperature was slowly increased to room temperature, thereby preparing an organozinc reagent. In another reaction vessel, the product A obtained in (1-1) in Example 1 (39.4 g) and tetrakis(triphenylphosphine)palladium (0) (2.5 g) were dissolved in THF (200 mL) under a nitrogen atmosphere, a solution of the organozinc reagent prepared as described above was added thereto, and the mixture was stirred for 10 hours at room temperature. Under cooling with ice, 10% hydrochloric acid (300 mL) was slowly added to the reaction solution, and toluene (300 mL) was added thereto to separate the organic layer. Toluene was added to the water layer for separation, and the organic layer was added thereto and washed three times with a saturated salt solution. Sodium sulfate was added thereto for dehydration, the product was purified by silica gel column chromatography, and the purified product was recrystallized from ethanol and hexane, thereby yielding a white solid that was [4-(3,5-difluoro-4-(5,6,7-trifluoronaphthalene-2-yl)phenyl)phenyl]-(2,6-difluoro-4-propylphenyloxy)methane (34.2 g).

MS m/z: 554[M+]

Example 5

Production of [4-(5,6,7-trifluoronaphthalene-2-yl)phenyl]-[2,6-difluoro-4-(trans-4-propylcyclohexyl)phenyloxy]methane

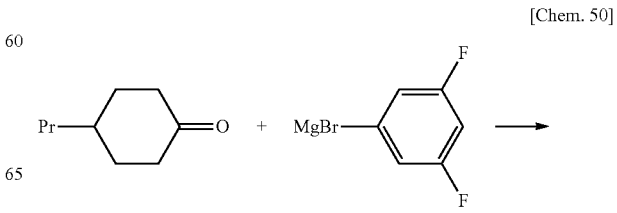

[Chem. 50]

-continued

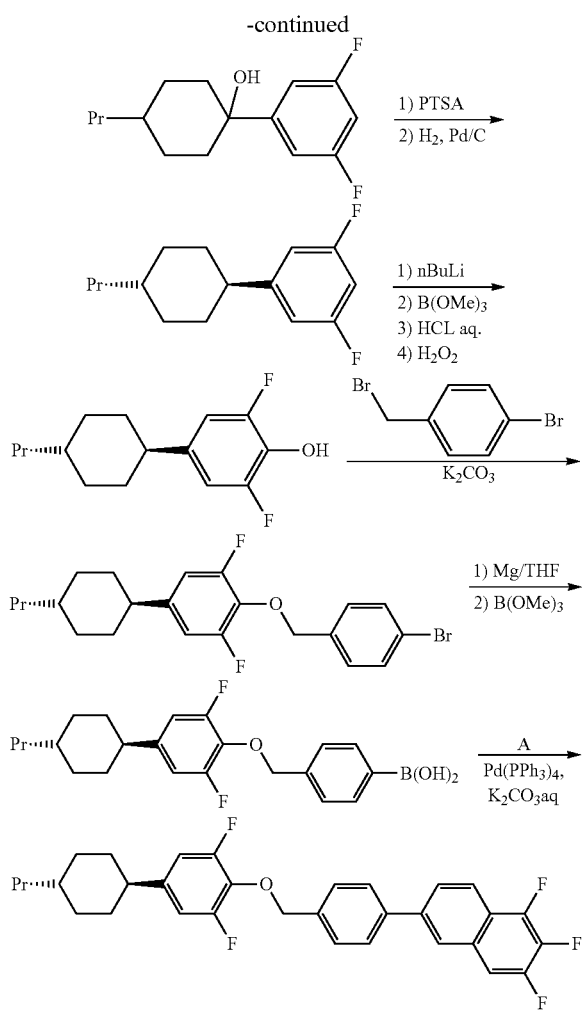

(5-1) Under a nitrogen atmosphere, at a rate which allowed moderate reflux, a solution in which 3,5-difluorobromobenzene (75.9 g) had been dissolved in THE (150 mL) was added to a suspension solution in which magnesium (10.0 g) had been mixed with THF (50 mL); then, the mixture was stirred for an hour at 40° C. The product was left to stand for cooling to room temperature, a solution in which 4-propylcyclohexanone (60.62 g) had been dissolved in THF (120 mL) was added thereto at a rate which did not allow the internal temperature to exceed 35° C., and the product was stirred for 2 hours at room temperature. Then, 10% hydrochloric acid was added thereto until the inside of the system entered an acid state in order to separate the organic layer. Toluene was added to the water layer for extraction, and the organic layer was added thereto and washed with a saturated salt solution. Sodium sulfate was added thereto for dehydration, and the solvent was distilled off under reduced pressure, thereby yielding crude 1-(1-hydroxy-4-propylcyclohexyl)-3,5-difluorobenzene (132 g).

(5-2) Under a nitrogen atmosphere, the crude 1-(1-hydroxy-4-propylcyclohexyl)-3,5-difluorobenzene (132 g) and p-toluenesulfonic acid monohydrate (2.99 g) were dissolved in toluene (250 mL), and the product was stirred for two hours under reflux while the generated water was removed. The product was left to stand for cooling to room temperature, the organic layer was washed with an aqueous saturated sodium hydrogen carbonate solution and a saturated salt solution, sodium sulfate was added thereto for dehydration, and the solvent was distilled off under reduced pressure. Then, the whole of the product was dissolved in ethyl acetate (280 mL), 5% palladium/carbon (7.1 g) was added thereto, and the product was stirred for 6 hours at 5 MPa under a hydrogen atmosphere. The palladium catalyst was separated by filtration, the solvent was distilled off under reduced pressure, and the product was purified by silica gel column chromatography. Then, the whole of the product and tert-butoxypotassium (3.4 g) were dissolved in DMF (350 mL), and the product was stirred for 4 hours at room temperature. Water and hexane were added thereto for separation, and the organic layer was separated. Hexane was added to the water layer for extraction, and the organic layer was added thereto and washed with a saturated salt solution. The sodium sulfate was added thereto for dehydration, the solvent was distilled off, and the product was distilled under reduced pressure (206 Pa, b. p.=110 to 112° C.), thereby yielding a colorless transparent liquid that was 1-(trans-4-propylcyclohexyl)-3,5-difluorobenzene (58.1 g).

(5-3) Under a nitrogen pressure, 1-(trans-4-propylcyclohexyl)-3,5-difluorobenzene (58.1 g) was dissolved in THF (300 mL), the solution was cooled to −40° C., and 1.6 mol/L of an n-butyllithium/hexane solution (170 mL) was added thereto at a rate which did not allow the internal temperature to exceed −35° C. The product was further stirred for an hour at −40° C., a solution in which trimethyl borate (30.4 g) had been dissolved in THF (100 mL) was added thereto at a rate which did not allow the internal temperature to be −35 or higher, the product was further stirred for an hour at −40° C., and then the internal temperature was increased to room temperature. The product was cooled with ice, 10% hydrochloric acid was subsequently added thereto until the inside of the system entered an acid state in order to separate the organic layer. The organic layer was cooled with ice, 15% aqueous hydrogen peroxide (60.8 g) was added thereto, and the product was heated to 40° C. and then further stirred for 15 hours. Unnecessary hydrogen peroxide was inactivated with an aqueous 10% sodium sulfite solution, then the organic layer was washed with a saturated salt solution, sodium sulfate was added thereto for dehydration, and the solvent was distilled off under reduced pressure. The product was purified by silica gel column chromatography, and the purified product was recrystallized from hexane, thereby yielding 2,6-difluoro-4-(trans-4-propylcyclohexyl)phenol (52.5 g).

(5-4) In this process, the reaction was performed as in Example 1 except that the 2,6-difluoro-4-(trans-4-propylcyclohexyl)phenol replaced 4-[(2,6-difluoro-4-propylphenyloxy)methyl]bromobenzene used in Example 1, thereby yielding a white solid that was [4-(5,6,7-trifluoronaphthalene-2-yl)phenyl]-[2,6-difluoro-4-(trans-4-propylcyclohexyl)phenyloxy]methane (54.4 g).

MS m/z: 524[M+]

Phase transition temperature (° C.): Cr 71 N 197 Iso $^1$HNMR (CDCl$_3$, TMS internal standard substance) δ (ppm)=8.11 (1H, d, J=8.80 Hz), 7.95 (1H, s), 7.80 (1H, d, J=8.80 Hz), 7.69 (2H, d, J=8.04 Hz), 7.59 (2H, d, J=8.04 Hz), 7.46-7.41 (1H, m), 6.75 (2H, d, J=9.6 Hz), 5.18 (2H, s), 2.42-2.36 (1H, m), 1.86 (4H, d, J=11 Hz), 1.40-1.17 (7H, m), 1.06-0.97 (2H, m), 0.90 (3H, t, J=7.28 Hz)

Example 6

[4-(5,6-difluoronaphthalene-2-yl)phenyl]-(2-fluoro-4-methylphenyloxy)methane

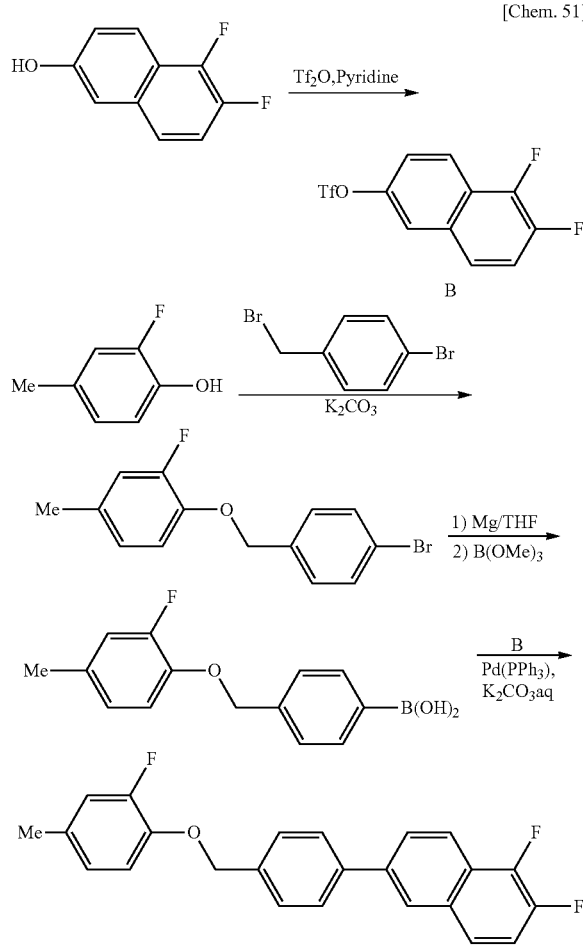

(6-1) Except that 5,6-difluoro-2-naphthol replaced the 5,6,7-trifluoro-2-naphthol used in (1-1) in Example 1, the reaction was performed as in Example 1-1, thereby yielding a colorless transparent liquid that was trifluoromethane sulfonic acid 5,6-difluoronaphthalene-2-yl (B, 34.3 g).

(6-2) Except that 2-fluoro-4-methylphenol replaced the 2,6-difluoro-4-propylphenol used in (4-1) in Example 4, etherification was performed as in Example 4-1, thereby yielding a slightly yellow liquid that was 4-[(2-fluoro-4-methylphenyloxy)methyl]bromobenzene (23.5 g).

(6-3) 4-[(2-fluoro-4-methylphenyloxy)methyl]bromobenezene was used instead of 4-[(2,6-difluoro-4-propylphenyloxy)methyl]bromobenzene used in (1-4) in Example 1. Other than the change above, the reaction was performed as in Example 1-4, thereby yielding a yellow liquid that was crude 4-[(2-fluoro-4-methylphenyloxy)methyl]phenylboronic acid (17.7 g).

(6-4) Except that 4-[(2-fluoro-4-methylphenyloxy)methyl]phenylboronic acid replaced the 4-[(2,6-difluoro-4-propylphenyloxy)methyl]phenylboric acid used in (1-5) in Example 1 and that the product B was used in place of the product A prepared in Example 1, the reaction was performed as in (1-5) in Example 1, thereby yielding a white solid that was [4-(5,6-difluoronaphthalene-2-yl)phenyl]-(2-fluoro-4-methylphenyloxy)methane (11.7 g).

MS m/z: 378 [M+]

Comparative Example 1

Production of 4-[4-(5,6,7-trifluoro-naphthalene-2-yl) 3-fluorophenyl]propylbenzene

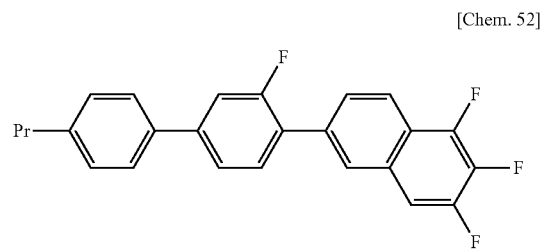

As disclosed in Japanese Unexamined Patent Application Publication No. 2000-355560, 4-[4-(5,6,7-trifluoro-naphthalene-2-yl) 3-fluorophenyl]propylbenzene was synthesized.

Example 7

Preparation-1 of Liquid Crystal Composition

A host liquid crystal composition (H) composed of the following components was prepared.

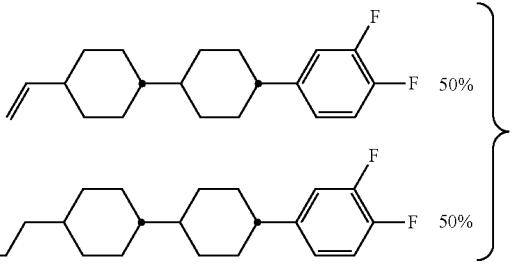

The liquid crystal composition (H) had the following physical properties.

Upper limit of temperature of nematic phase ($T_{n-i}$): 117.2° C.

Dielectric anisotropy (Δ∈): 4.38

Refractive index anisotropy (Δn): 0.0899

Viscosity (η20): 20.3 mPa·s

A liquid crystal composition (M-A) composed of the host liquid crystal (H) of 80% and [4-(5,6,7-trifluoronaphthalene-2-yl)phenyl]-(2,6-difluoro-4-propylphenyloxy)methane, which had been obtained in Example 1, of 20% was prepared. This composition had the following physical properties.

$T_{n-i}$: 106.6° C.

Δ∈: 9.20

Δn: 0.1132

$\eta_{20}$: 25.9 mPa·s

Use of the [4-(5,6,7-trifluoronaphthalene-2-yl)phenyl]-(2,6-difluoro-4-propylphenyloxy)methane gave the following effects: relatively small decrease in $T_{n-i}$ (extrapolated $T_{n-i}$=65.6° C.), positive increase in $\Delta\varepsilon$ (extrapolated $\Delta\varepsilon$=28.5), large increase in $\Delta n$ (extrapolated $\Delta n$=0.206), and relatively suppressed increase in viscosity (extrapolated $\eta_{20}$=48.3 mPa·s). The prepared liquid crystal composition (M-A) continued to be in a homogeneous state of nematic liquid crystal for a month or longer at room temperature, which showed that good miscibility was exhibited in the liquid crystal composition.

Example 8

Preparation-2 of Liquid Crystal Composition

A liquid crystal composition (M-B) composed of the host liquid crystal (H) of 95% and the trans-4-(4-(5,6,7-trifluoronaphthalene-2-yl)-3,5-difluorophenyl)cyclohexyl)-(2,6-difluoro-4-propylphenyloxy)methane, which had been prepared in Example 3, of 5% was prepared. This composition had the following physical properties.

$T_{n-i}$: 117.9° C.
$\Delta\varepsilon$: 5.93
$\Delta n$: 0.0949
$\eta_{20}$: 23.8 mPa·s Use of the trans-4-(4-(5,6,7-trifluoronaphthalene-2-yl)-3,5-difluorophenyl)cyclohexyl)-(2,6-difluoro-4-propylphenyloxy)methane gave the following effects: increase in $T_{n-i}$ (extrapolated $T_{n-i}$=137.9° C.), positive increase in $\Delta\varepsilon$ (extrapolated $\Delta\varepsilon$=33.9), large increase in $\Delta n$ (extrapolated $\Delta n$=0.237), and relatively suppressed increase in viscosity (extrapolated $\eta_{20}$=101.1 mPa·s). The prepared liquid crystal composition (M-B) continued to be in a homogeneous state of nematic liquid crystal for a month or longer at room temperature, which showed that good miscibility was exhibited in the liquid crystal composition.

Example 9

Preparation-3 of Liquid Crystal Composition

A liquid crystal composition (M-C) composed of the host liquid crystal (H) of 80% and the [4-(5,6,7-trifluoronaphthalene-2-yl)phenyl]-[2,6-difluoro-4-(trans-4-propylcyclohexyl)phenyloxy]methane, which had been obtained in Example 5, of 20% was prepared. This composition had the following physical properties.

$T_{n-i}$: 130.8° C.
$\Delta\varepsilon$: 8.10
$\Delta n$: 0.1131
$\eta_{20}$: 30.5 mPa·s Use of the [4-(5,6,7-trifluoronaphthalene-2-yl)phenyl]-[2,6-difluoro-4-(trans-4-propylcyclohexyl)phenyloxy]methane gave the following effects: large increase in $T_{n-i}$ (extrapolated $T_{n-i}$=186.6° C.), positive increase in $\Delta\varepsilon$ (extrapolated $\Delta\varepsilon$=22.7), large increase in $\Delta n$ (extrapolated $\Delta n$=0.216), and relatively suppressed increase in viscosity (extrapolated $\eta_{20}$=73.7 mPa·s). The prepared liquid crystal composition (M-C) continued to be in a homogeneous state of nematic liquid crystal for a month or longer at room temperature, which showed that good miscibility was exhibited in the liquid crystal composition.

Comparative Example 2

Preparation-2 of Liquid Crystal Composition

A liquid crystal composition (M-D) composed of the host liquid crystal (H) of 85% and the 4-[4-(5,6,7-trifluoro-naphthalene-2-yl) 3-fluorophenyl]propylbenzene, which had been obtained in Comparative Example 1, of 15% was prepared. This composition had the following physical properties.

$T_{n-i}$: 120.6° C.
$\Delta\varepsilon$: 7.10
$\Delta n$: 0.1208
$\eta_{20}$: 26.0 mPa·s Use of the 4-[4-(5,6,7-trifluoro-naphthalene-2-yl)3-fluorophenyl]propylbenzene gave the following effects: increase in $T_{n-i}$ (extrapolated $T_{n-i}$=139.9° C.), positive increase in $\Delta\varepsilon$ (extrapolated $\Delta\varepsilon$=22.5), great increase in $\Delta n$ (extrapolated $\Delta n$=0.296), and relatively suppressed increase in viscosity (extrapolated $\eta_{20}$=58.2 mPa·s). In the prepared liquid crystal composition (M-D), however, crystals precipitated after storage thereof for three days at room temperature, which showed that relatively low miscibility with the host liquid crystal was exhibited.

As is clear from comparison between Example 7 and Comparative Example 2, $T_{n-i}$ and $\Delta n$ were smaller in the compound of the present invention than in the comparative compound; however, the compound of the present invention had a sufficiently large $\Delta\varepsilon$ and an effect in which an increase in viscosity was greatly suppressed. Since the proportion of the compound to the host liquid crystal differed between Example 7 and Comparative Example 1, Example 7 and Comparative Example 2 were compared with reference to extrapolated values based on assumption that the concentration was 100%. In addition, the liquid crystal composition containing a compound represented by Formula (1) exhibited a stable nematic phase for a long time.

The invention claimed is:
1. A method for producing a compound represented by Formula (1), the method comprising:
allowing a compound represented by Formula (2) to react with a compound represented by Formula (3) to derive a compound represented by Formula (4)

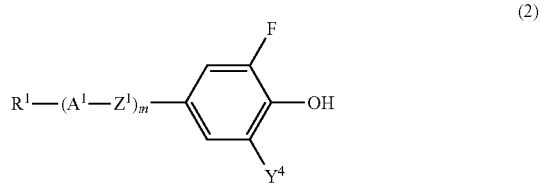

(where $R^1$ represents an alkyl group having 1 to 15 carbon atoms or an alkenyl group having 2 to 15 carbon atoms in which one —$CH_2$— moiety or at least two —$CH_2$— moieties not adjoining each other are each independently optionally substituted with —O—, —S—, —COO—, —OCO—, or —CO—, $A^1$ is a group selected from the group consisting of
(a) a 1,4-cyclohexylene group (where one —$CH_2$— moiety or at least two —$CH_2$— moieties not adjoining each other are each independently optionally substituted with O— or —S—) and
(b) a 1,4-phenylene group (where one —CH═ moiety or at least two —CH═ moieties not adjoining each other are optionally substituted with —N═, and a hydrogen atom is optionally substituted with a fluorine atom),
$Z^1$ represents —$CH_2O$—, —$OCH_2$—, —$CF_2O$—, —$OCF_2$—, —$CH_2CH_2$—, —$CF_2CF_2$—, —CH═CH—, —CF═CF—, —C≡C—, or a single bond, $Y^4$ represents a hydrogen atom, a fluorine atom, or a chlorine atom, and m represents 0 or 1)

(where $A^2$ represents the same as $A^1$ in Formula (2), $A^3$ represents a 1,4-phenylene group (where a hydrogen atom is optionally substituted with a fluorine atom), $X^1$ represents a hydroxyl group, a chlorine atom, a bromine atom, an iodine atom, a tosyloxy group, a mesyloxy group, or a trifluoromethanesulfonyloxy group, $X^2$ represents a chlorine atom, a bromine atom, or an iodine atom or is optionally a hydrogen atom in the case where $A^3$ is a group selected from (A-1) or (A-2)

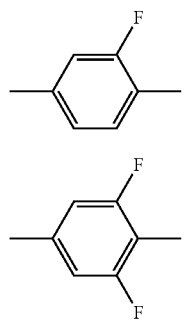

$Z^2$ represents the same as $Z^1$ in Formula (2), and n represents 0 or 1)

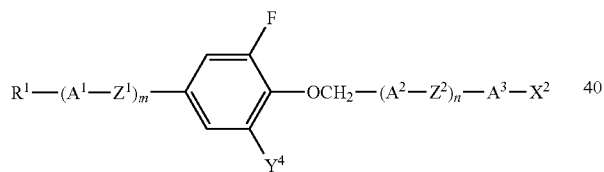

(where $R^1$, $A^1$, $A^2$, $A^3$, $Z^1$, $Z^2$, m, n, $Y^4$, and $X^2$ each independently represent the same as $R^1$, $A^1$, $A^2$, $A^3$, $Z^1$, $Z^2$, m, n, $Y^4$, and $X^2$ in Formula (2) or Formula (3));

allowing the compound represented by Formula (4) to react with metal or organic metal and optionally further substituting a metal of a prepared organometallic compound with another atom to prepare a compound represented by Formula (5)

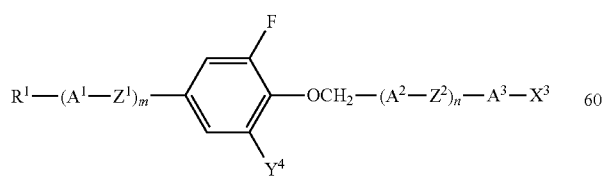

(where $R^1$, $A^1$, $A^2$, $A^3$, $Z^1$, $Z^2$, m, n, and $Y^4$ each independently represent the same as $R^1$, $A^1$, $A^2$, $A^3$, $Z^1$, $Z^2$, m, n, and $Y^4$ in Formula (4), and $X^3$ represents $MgX^4$, Li, Na, $ZnX^4$, or $CuX^4$ (where $X^4$ represents a chlorine atom, a bromine atom, or an iodine atom) or represents a substituent represented by Formula (B-1) or (B-2)

(where $R^2$ and $R^3$ each independently represent a linear or branched alkyl group having 1 to 5 carbon atoms, E represents —$(CH_2)_p$— in which one or more hydrogen atoms are each independently optionally substituted with a methyl group, and p represents 2, 3, or 4)); and allowing the compound represented by Formula (5) to react with a compound represented by Formula (6)

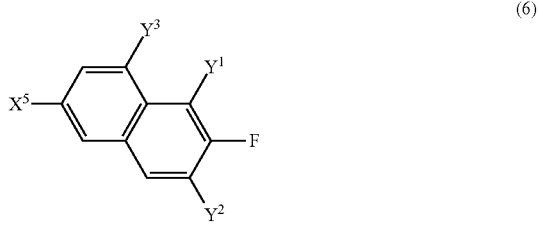

(where $Y^1$, $Y^2$, and $Y^3$ each independently represent a hydrogen atom, a fluorine atom, or a chlorine atom, and $X^5$ represents a trifluoromethanesulfonyloxy group, a chlorine atom, a bromine atom, or an iodine atom) in the presence of a transition metal catalyst

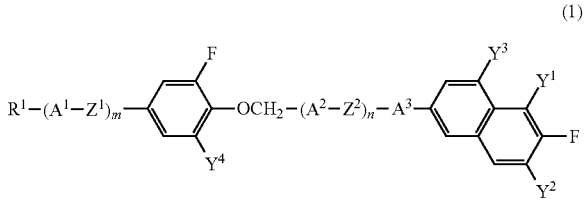

(where $R^1$, $A^1$, $A^2$, $A^3$, $Z^1$, $Z^2$, m, n, $Y^1$, $Y^2$, $Y^3$, and $Y^4$ each independently represent the same as $R^1$, $A^1$, $A^2$, $A^3$, $Z^1$, $Z^2$, m, n, $Y^1$, $Y^2$, $Y^3$, and $Y^4$ in Formula (5) or (6)), wherein in the case where $X^1$ is a hydroxyl group, the reaction of the compound represented by Formula (2) with the compound represented by Formula (3) is condensation in the presence of a dehydrating condensation agent, and in the case where $X^1$ is a chlorine atom, a bromine atom, an iodine atom, a tosyloxy group, a mesyloxy group, or a trifluoromethanesulfonyloxy group, the reaction is an etherification reaction in the presence of a base.

2. The method according to claim 1, wherein the compound represented by Formula (4) is allowed to react with an alkali metal, an alkaline earth metal, or an organolithium to prepare the compound represented by Formula (5).

3. The method according to claim 1, wherein the compound represented by Formula (2) is condensed with the compound represented by Formula (3) with the aid of azodicarboxylic acid as a dehydrating condensation agent and further with the aid of a phosphine to prepare the compound represented by Formula (4).

4. The method according to claim 1, wherein the compound represented by Formula (2) is etherified with the compound represented by Formula (3) with the aid of an alkali metal hydroxide, alkaline earth metal hydroxide, or alkali metal carbonate as a base to prepare the compound represented by Formula (4).

5. The method according to claim 1, wherein the compound represented by Formula (4) in which $X^2$ is a chlorine atom, a bromine atom, or an iodine atom is allowed to react with a metallic lithium, a metallic sodium, a magnesium metal, n-butyllithium, sec-butyllithium, or tert-butyllithium to prepare a compound represented by Formula (5) in which $X^3$ represents $MgX^4$, Li, or Na (where $X^4$ represents a chlorine atom, a bromine atom, or an iodine atom), and the prepared compound is further allowed to react with a borate ester to produce a compound represented by Formula (5) in which $X^3$ is a functional group represented by Formula (B-1) or (B-2).

6. The method according to claim 1, wherein the compound represented by Formula (4) in which $X^2$ is a hydrogen atom is allowed to react with n-butyllithium, sec-butyllithium, tert-butyllithium, or diisopropyl lithium amide to prepare a compound represented by Formula (5) in which $X^3$ represents Li, and the prepared compound is further allowed to react with a borate ester to produce a compound represented by Formula (5) in which $X^3$ is a functional group represented by Formula (B-1) or (B-2).

7. The method according to claim 1, wherein the compound represented by Formula (5) is allowed to react with the compound represented by Formula (6) with the aid of a palladium-based transition metal catalyst or a nickel-based transition metal catalyst as a transition metal catalyst and further with the aid of a base to prepare the compound represented by Formula (1).

8. A compound represented by Formula (1)

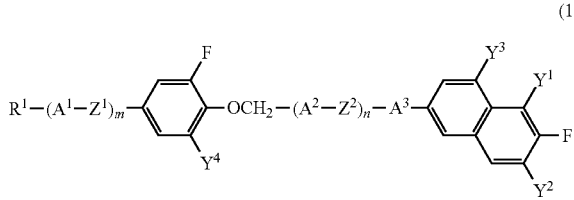

(1)

(where $R^1$ represents an alkyl group having 1 to 15 carbon atoms or an alkenyl group having 2 to 15 carbon atoms in which one —$CH_2$— moiety or at least two —$CH_2$— moieties not adjoining each other are each independently optionally substituted with —O—, —S—, —COO—, —OCO—, or —CO—, $A^1$ and $A^2$ are each independently a group selected from the group consisting of
(a) a 1,4-cyclohexylene group (where one —$CH_2$— moiety or at least two —$CH_2$— moieties not adjoining each other are each independently optionally substituted with O— or —S—) and
(b) a 1,4-phenylene group (where one —CH= moiety or at least two —CH= moieties not adjoining each other are optionally substituted with —N=, and a hydrogen atom is optionally substituted with a fluorine atom), $A^3$ represents a 1,4-phenylene group (where a hydrogen atom is optionally substituted with a fluorine atom), $Z^1$ and $Z^2$ each independently represent —$CH_2O$—, —$OCH_2$—, —$CF_2O$—, —$OCF_2$—, —$CH_2CH_2$—, —$CF_2CF_2$—, —CH=CH—, —CF=CF—, —C≡C—, or a single bond, $Y^1$, $Y^2$, $Y^3$, and $Y^4$ each independently represent a hydrogen atom, a fluorine atom, or a chlorine atom, and m and n each independently represent 0 or 1).

9. The compound according to claim 8, wherein $A^3$ in Formula (1) represents a group selected from the following groups

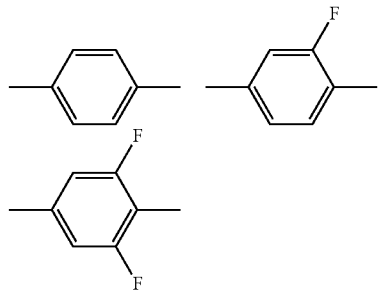

10. The compound according to claim 8, wherein $Y^4$ in Formula (1) represents a fluorine atom.

11. The compound according to claim 8, wherein $Y^3$ in Formula (1) represents a hydrogen atom.

12. The compound according to claim 8, wherein $Y^1$ and $Y^2$ in Formula (1) each represent a fluorine atom.

13. The compound according to claim 8, wherein m in Formula (1) represents 0.

14. The compound according to claim 8, wherein n in Formula (1) represents 1.

15. The compound according to claim 10, wherein n in Formula (1) represents 0.

16. A liquid crystal composition comprising at least one of the compounds according to claim 8.

17. A liquid crystal device comprising the liquid crystal composition according to claim 16.

* * * * *